(12) United States Patent
Wisnewski et al.

(10) Patent No.: US 7,476,728 B2
(45) Date of Patent: Jan. 13, 2009

(54) FLEA GABA RECEPTOR SUBUNIT NUCLEIC ACID MOLECULES

(75) Inventors: Nancy Wisnewski, Fort Collins, CO (US); Kevin S. Brandt, Fort Collins, CO (US)

(73) Assignee: Heska Corporation, Loveland, CO (US)

( * ) Notice: Subject to any disclaimer, the term of this patent is extended or adjusted under 35 U.S.C. 154(b) by 583 days.

(21) Appl. No.: 10/433,140

(22) PCT Filed: Nov. 21, 2002

(86) PCT No.: PCT/US01/44082

§ 371 (c)(1),
(2), (4) Date: May 30, 2003

(87) PCT Pub. No.: WO02/44374

PCT Pub. Date: Jun. 6, 2002

(65) Prior Publication Data

US 2004/0091894 A1    May 13, 2004

(51) Int. Cl.
*C07H 21/02* (2006.01)
(52) U.S. Cl. .................................. 536/23.1
(58) Field of Classification Search ...................... None
See application file for complete search history.

(56) References Cited

U.S. PATENT DOCUMENTS

| 6,008,046 | A | 12/1999 | Ffrench-Constant et al. | |
|---|---|---|---|---|
| 6,329,516 | B1 * | 12/2001 | Halling et al. | 536/23.5 |
| 6,358,701 | B1 * | 3/2002 | Warmke et al. | 435/69.1 |

FOREIGN PATENT DOCUMENTS

WO    WO 98/49185    11/1998

OTHER PUBLICATIONS

Vassilatis et al. Evolutionary Relationship of the Ligand-Gated Ion Channels and the Avermectin-Sensitive, Glutamate-Gated Chloride Channels. Journal of Molecular Evolution, 1997. 44:501-508.*
ffrench-Constant (Why are there so few resistance-associated mutations in insecticide target genes? Pil. Trans. R. Soc. Lond., 1998. 353:1685-1693).*
Bloomquist (Chloride Channels as Tools for Developing Selective Insecticides. Archives of Insect Biochemistry and Physiology, 2003. 54:145-156).*
Buckingham (Insect GABA Receptors: Splicing, Editing, and Targeting by Antiparasitics and Insecticides. Molecular Pharmacology, 2005. 942-951).*
Anthony, et al., 1993, *Comparative Molecular Neurobiology*, vol. 63, pp. 172-209, XP-001119720.
Anonymous, 1997, *Research Disclosure, Kenneth Mason Publications*, No. 403, p. 837, XP000726741.
Casida, John E., 1993, *Archives of Insect Biochemistry and Physiology*, vol. 22, pp. 13-23.
Chen, et al., 2000, Database Accession No. Q9VSVO, XP-002220419.
Cole, et al., 1993, *Pesticide Biochemistry and Physiology*, vol. 46, pp. 47-54.
Ffrench-Constant, et al., 1991, *Proc. Natl. Acad. Sci. USA*, vol. 88, pp. 7209-7213, XP-002220410.
Ffrench-Constant, et al., 2000, *Annu. Rev. Entomolo.*, vol. 48, pp. 449-466.
Glueck, et al., 1998, Database Accession No. O17145, XP002220417.
Glueck, et al., 1998, Database Accession No. AF094822, XP-002220415,
Hook-d'Innocenzo, et al., 2000, Database Accession No. Q9U9B8, XP-002220416.
Hosie, et al., 1997, *Trends Neurosci.*, vol. 20, pp. 578-583.
Pritchett, et al., 1989, *Letters to Nature*, vol. 338, pp. 582-585.
Thompson, et al., 1993, *FEBS Letters*, vol. 325, No. 3, pp. 187-190, XP-002220411.
Thompson, et al., 1993, *Insect Molecular Biology*, vol. 2, No. 3, pp. 149-154.
Wingate, et al., 2000, Database Accession No. A94237, XP-002220418.

* cited by examiner

*Primary Examiner*—David Guzo
*Assistant Examiner*—Michele K. Joike

(57) ABSTRACT

The present invention relates to flea GABA receptor subunit nucleic acid molecules; to flea GABA receptor subunit proteins encoded by such nucleic acid molecules; to antibodies raised against such proteins; and to compounds that inhibit the activity of such proteins. The present invention also includes methods to obtain such proteins, nucleic acid molecules, antibodies, and inhibitory compounds. The present invention also includes therapeutic compositions comprising such proteins, nucleic acid molecules, antibodies and inhibitory compounds, particularly those that specifically inhibit flea GABA receptor subunit activity, as well as the use of such therapeutic compositions to treat animals.

4 Claims, No Drawings

SEQUENCE LISTING

<160> NUMBER OF SEQ ID NOS: 20

<210> SEQ ID NO 1
<211> LENGTH: 183
<212> TYPE: DNA
<213> ORGANISM: Ctenocephalides felis
<220> FEATURE:
<221> NAME/KEY: CDS
<222> LOCATION: (2)..(181)

<400> SEQUENCE: 1

```
a ttc ttc gta aac gag aaa caa tct tac ttc cac atc gca acc acc agc        49
  Phe Phe Val Asn Glu Lys Gln Ser Tyr Phe His Ile Ala Thr Thr Ser
  1               5                   10                  15 aac gag ttc ata cga atc cac cac tct ggt tcc atc acg agg agc ata        97
Asn Glu Phe Ile Arg Ile His His Ser Gly Ser Ile Thr Arg Ser Ile
            20                  25                  30 cgg ctg acg atc act gcc tca tgt cca atg aat ctt caa tac ttc cct       145
Arg Leu Thr Ile Thr Ala Ser Cys Pro Met Asn Leu Gln Tyr Phe Pro
        35                  40                  45 atg gac aga caa ctt tgt cac ata gaa atc gag agc tt                    183
Met Asp Arg Gln Leu Cys His Ile Glu Ile Glu Ser
    50                  55                  60
```

<210> SEQ ID NO 2
<211> LENGTH: 60
<212> TYPE: PRT
<213> ORGANISM: Ctenocephalides felis

<400> SEQUENCE: 2

```
Phe Phe Val Asn Glu Lys Gln Ser Tyr Phe His Ile Ala Thr Thr Ser
1               5                   10                  15

Asn Glu Phe Ile Arg Ile His His Ser Gly Ser Ile Thr Arg Ser Ile
            20                  25                  30
```

-continued

```
                Arg Leu Thr Ile Thr Ala Ser Cys Pro Met Asn Leu Gln Tyr Phe Pro
                        35                  40                  45

Met Asp Arg Gln Leu Cys His Ile Glu Ile Glu Ser
                50                  55                  60

<210> SEQ ID NO 3
<211> LENGTH: 183
<212> TYPE: DNA
<213> ORGANISM: Ctenocephalides felis

<400> SEQUENCE: 3
aagctctcga tttctatgtg acaaagttgt ctgtccatag ggaagtattg aagattcatt      60
ggacatgagg cagtgatcgt cagccgtatg ctcctcgtga tggaaccaga gtggtggatt    120
cgtatgaact cgttgctggt ggttgcgatg tggaagtaag attgtttctc gtttacgaag    180
aat                                                                  183

<210> SEQ ID NO 4
<211> LENGTH: 5503
<212> TYPE: DNA
<213> ORGANISM: Ctenocephalides felis
<220> FEATURE:
<221> NAME/KEY: CDS
<222> LOCATION: (378)..(1823)

<400> SEQUENCE: 4
cgtacacctt cggcacacgt aacaaacgtc aactgtcaac tgtttcgaac acgcgcgcgt      60
tctgtcgtcc dataggtact gatttgattt caattgtaga dacatatttt gacaaatttg    120
gacactgaca gctctgcgta cgtaaagttc gtttaaaaac tttgttcgat aagtattaca    180
agcgcctata aagcaagttg gaaataaatt tgctgcaaac tgaaataaac cagacgatca    240
agtcgtcacg gtgtgcacct atcatattat tattaattgt gtgtgaaatg tccgtcaagg    300
acatgtaaca tcgagcccca aatgaagaat ccgggccgtc ggtgagatgc gccaggggcg    360
gctggtgtag cgggggc atg gcg gcg ctg act cgc gca acc atg ggg gcc       410
                    Met Ala Ala Leu Thr Arg Ala Thr Met Gly Ala
                      1               5                  10 ctc ctg ctg gcc ctc agt ccg gcc ctg ttg ctg ata tgg cta ccg tac      458
Leu Leu Leu Ala Leu Ser Pro Ala Leu Leu Leu Ile Trp Leu Pro Tyr
             15                  20                  25 gcg gat gcc gcg acg ggg ggc ggc agt atg tac ggc gac gtc aac att      506
Ala Asp Ala Ala Thr Gly Gly Gly Ser Met Tyr Gly Asp Val Asn Ile
         30                  35                  40 tct gcc atc ttg gat aac ttc agc gtc agc tac gac aaa aga gta aga      554
Ser Ala Ile Leu Asp Asn Phe Ser Val Ser Tyr Asp Lys Arg Val Arg
     45                  50                  55 ccg aat tat gga gga cct cca gtg gaa gtt ggt gtc acg atg tac gtc      602
Pro Asn Tyr Gly Gly Pro Pro Val Glu Val Gly Val Thr Met Tyr Val
60                  65                  70                  75 ctc tcc atc agt tcg ctg tcc gaa gtc aaa atg gac ttc acg ctg gac      650
Leu Ser Ile Ser Ser Leu Ser Glu Val Lys Met Asp Phe Thr Leu Asp
                 80                  85                  90 ttt tac ttt cgg caa ttc tgg acg gat ccg cgg cta gcg tac agg aaa      698
Phe Tyr Phe Arg Gln Phe Trp Thr Asp Pro Arg Leu Ala Tyr Arg Lys
             95                 100                 105 cgt ccc ggt gtc gaa acg ctt tct gtg ggt tcc gag ttt att aaa aac      746
Arg Pro Gly Val Glu Thr Leu Ser Val Gly Ser Glu Phe Ile Lys Asn
        110                 115                 120 ata tgg gtc cct gac aca ttc ttc gta aac gag aaa caa tct tac ttc      794
Ile Trp Val Pro Asp Thr Phe Phe Val Asn Glu Lys Gln Ser Tyr Phe
```

-continued

```
           125                 130                 135
cac atc gca acc acc agc aac gag ttc ata cga atc cac cac tct ggt        842
His Ile Ala Thr Thr Ser Asn Glu Phe Ile Arg Ile His His Ser Gly
140                 145                 150                 155 tcc atc acg agg agc ata cgg ctg acg atc act gcc tca tgt cca atg        890
Ser Ile Thr Arg Ser Ile Arg Leu Thr Ile Thr Ala Ser Cys Pro Met
                160                 165                 170 aat ctt caa tac ttc cct atg gac aga caa ctt tgt cac ata gaa atc        938
Asn Leu Gln Tyr Phe Pro Met Asp Arg Gln Leu Cys His Ile Glu Ile
            175                 180                 185 gag agc ttc ggc tac acg atg cgc gat att cga tat aag tgg aac gaa        986
Glu Ser Phe Gly Tyr Thr Met Arg Asp Ile Arg Tyr Lys Trp Asn Glu
        190                 195                 200 gga ccg aac tca gtg ggg gtc tct aac gag gtg tcg ctg ccg caa ttc       1034
Gly Pro Asn Ser Val Gly Val Ser Asn Glu Val Ser Leu Pro Gln Phe
    205                 210                 215 aaa gtc ctg gga cat cga caa cga gca atg gag atc agt ctc aca aca       1082
Lys Val Leu Gly His Arg Gln Arg Ala Met Glu Ile Ser Leu Thr Thr
220                 225                 230                 235 gga aac tat tct cgc ctg gcg tgc gag att caa ttc gtg cgt tct atg       1130
Gly Asn Tyr Ser Arg Leu Ala Cys Glu Ile Gln Phe Val Arg Ser Met
                240                 245                 250 ggc tac tac ctc atc caa atc tac att ccg tct ggt ctt atc gtg atc       1178
Gly Tyr Tyr Leu Ile Gln Ile Tyr Ile Pro Ser Gly Leu Ile Val Ile
            255                 260                 265 ata tcg tgg gta tcg ttt tgg ctg aat cgt aat gct aca cca gct cga       1226
Ile Ser Trp Val Ser Phe Trp Leu Asn Arg Asn Ala Thr Pro Ala Arg
        270                 275                 280 gtc tct ctc gga gtg acc act gtg ttg acc atg aca act cta atg tca       1274
Val Ser Leu Gly Val Thr Thr Val Leu Thr Met Thr Thr Leu Met Ser
    285                 290                 295 tcg aca aac gcc gcg cta cca aaa ata tca tac gtc aaa tct ata gac       1322
Ser Thr Asn Ala Ala Leu Pro Lys Ile Ser Tyr Val Lys Ser Ile Asp
300                 305                 310                 315 gtc tac ctg ggc acc tgt ttc gta atg gtg ttc gct agt tta tta gaa       1370
Val Tyr Leu Gly Thr Cys Phe Val Met Val Phe Ala Ser Leu Leu Glu
                320                 325                 330 tat gcc act gtt ggc tac atg gct aag cgc atc cat atg aga aaa cag       1418
Tyr Ala Thr Val Gly Tyr Met Ala Lys Arg Ile His Met Arg Lys Gln
            335                 340                 345 agg ttc atg gcg att cag aaa att gca gaa caa aag aaa cta caa gct       1466
Arg Phe Met Ala Ile Gln Lys Ile Ala Glu Gln Lys Lys Leu Gln Ala
        350                 355                 360 gaa ggc ggc ggg cca gga ggc ccc ggc gat cat tcc cat gcg ccc aaa       1514
Glu Gly Gly Gly Pro Gly Gly Pro Gly Asp His Ser His Ala Pro Lys
    365                 370                 375 caa aca gtg cgg ttc aag gtt cgc gac ccg aag gcg cat tcc aag ggc       1562
Gln Thr Val Arg Phe Lys Val Arg Asp Pro Lys Ala His Ser Lys Gly
380                 385                 390                 395 ggc acc ctc gag aac aca atc aac ggg ggg cga ggc ggg gcg gcc gcc       1610
Gly Thr Leu Glu Asn Thr Ile Asn Gly Gly Arg Gly Gly Ala Ala Ala
                400                 405                 410 gac gag gag agc gcc gcg cca gcg ccc caa cac ctc atc cac ccc ggc       1658
Asp Glu Glu Ser Ala Ala Pro Ala Pro Gln His Leu Ile His Pro Gly
            415                 420                 425 aag gac atc aac aag ctg ctc ggt atc act ccg tcg ggc atc gac aag       1706
Lys Asp Ile Asn Lys Leu Leu Gly Ile Thr Pro Ser Gly Ile Asp Lys
        430                 435                 440 tac tcg cgc atc gtg ttc ccg gtc tgc ttc gtt tgc ttc aac ttg atg       1754
Tyr Ser Arg Ile Val Phe Pro Val Cys Phe Val Cys Phe Asn Leu Met
```

```
                    Tyr Ser Arg Ile Val Phe Pro Val Cys Phe Val Cys Phe Asn Leu Met
                        445                 450                 455 tac tgg atc atg tat ctg cac gtg agc gac gtg gtg gcc gac gac ctg         1802
Tyr Trp Ile Met Tyr Leu His Val Ser Asp Val Val Ala Asp Asp Leu
460                 465                 470                 475 gtg ctc ctg gga gaa gac aaa tagagggcgc ccccagtatg cactcccata            1853
Val Leu Leu Gly Glu Asp Lys
                480 ctcaatccgt tgcctattgt aattgatcac tatggtttct taaaaaatcc catatcattt       1913 ttttacttat tcttaatcta tcagaaacct tcacctgtta tgttcgatcc aattgtagaa       1973 ttatacacct atatcccttc tgcaacattt gggcatggga aagcgcggt tctcgcaacc        2033 gcccgagcgt cggctcttgc cacgtacggg tcgaatgtta cgcgggaacc actgagggca       2093 cccggttaag actctcgggt acgggctgac gggacgctgg gtctccgcgc ccctgcatcg       2153 gcaggacatg atccaattgc cagaacgaga tcaggcagac gacagacaaa acaatgtcgg       2213 gcacataaaa cgcaaaatat tcgatcgcgc gacgttgccg atgtagcgag cagctgcact       2273 aaacacgtgt gttgtcccgg accgaggcgg gtggtgcata gagcgtgtga cgcgaggttt       2333 cccccttgtt ttcgcgtcat cttgtcgtga cgggatcgcc acttgtttgt tcttgggccc      2393 gtacgggagt actcgatgcg gacattctcc actttgcgcg acggataatt caagacacag       2453 aagaaaggag caacaaaggc atcggtgata tattctgaac ggttttatta ttcctgacat       2513 ataactatat aaactatata tatatacaca aatgcataaa tgataaatga aaagggtgta       2573 tcgtgcccgt atgtagcatt ccttattata tgtatgaac cccgttccaa ttattaattg        2633 tatgaatata taatatagca taaataacta tgatactaaa gagatcacag ataccaaaca       2693 agaaatataa gcacatgagt tcgttacgtg tgtaagcaaa ttgtcggccg atcgggctag       2753 aaatcattcc atctcgcatc acgtagggtt tatatttgta ccattaattc gctcactcac       2813 acatactcac acgtatatta agataagttg tcacctggta tcgcacttcg tatgtataga       2873 gataccgtaa gccgccaacg acagtgttga cttagactaa tgaatcgcgt caagtcgcat       2933 ctcagaaata gagtaaactt tacatttgaa tgaattttag tttacacaac aataaataaa       2993 attgcacatt catgtaacgt aatatagtag acagaatgct gttttatac ttccaatttt        3053 tcaatctagc cacaagagta ataatattca cacccagta ttcaaagtat tcaattggat        3113 gaatttccat tagcactaat gcgaacatat tttaaaccaa aaattaaggc ttcgacaacg       3173 acgacatgct aagtggttcc acataaaata gttctatggt ccacaaaaaa tgttatcgtt       3233 ttattactgt cttgtttaag aaatttagtg ttctatacta tctttagaaa cggtagtgat       3293 ggtttcgtgt ataggata caaagcattg tgatcaaaga attcaaatca ttgtttgata         3353 aatatactaa tacaatggat atctcttctt ccatttgtct tcaaataaag agtttactat       3413 atatttatat ccgatgatgc gactcgtagc taagaaaact atgatataat ttagagtctc      3473 gcaagggcgg gcgtactggg cggcattgcg acggattcgg aatacgccca gtatgccggt      3533 tcggatgagg cgaacaagaa attctaaact gatattaatt ataagataag gttaaagata      3593 tttaagtaca tatatataca agcatatgtt aacaaagtaa taggaaacat aacgtacgtt      3653 acgaacattc gtagtaaata tataaaata tataaaagca tatatgcaaa ttgcaaaaaa       3713 acttgtgtta tacaattatg acaccgtagc cttggaaggt atctaatttt ggtcattata       3773 aaacatacct tatgttactt ttaaaataag tattattgta aaaatcgcat tggcaatttt       3833 attatttcat attatatatt tagttttgat agataacaga atattgatag agtgcattta       3893
```

```
ctcaaaattg cttttagttg aaattttatt tacatatgta aaactttaa aaaaaaaatt    3953 atttattagt aaatatgcta tatcataact taaattagat actaaccaat aaaattttat    4013
gtttatataa ctattatgaa aaaaatgtat ttaatcagaa agaaaacata tataatatat    4073
attacatgta cagaacaatg aattaacata aaatgagaaa atgatagtga aatcgtttaa    4133
cgattattga tgatatataa acatatagac ttattgttat atatatatta aaatattaaa    4193
ataatatatt aggtacgtta tatttaaaat gtttatttga taccccgtaa tatataaaac    4253
aacaattaaa attatttgtt aaattttatt caagcagacg attaattcat tgtcttaaaa    4313
acatttatgg tatagacaaa tagaatattg ttaaacaact tattttttgca ttctattttt    4373 atcgtaatga tatggttaat aatgttatgt ttaaatattt taagaataaa taacattatt    4433
tatttgttaa taattagcat ttcctcaaaa ctatttgtct atattttgt attcattttc    4493 taattcaatt agattaaaac catcggcaaa gcgacgcttg aaaatatcaa atcgtttaat    4553
gtttcatcaa tataacaaaa tcaaaaaatt aaagcgtcta ttgtataaaa tgaaaatcat    4613 gaacaattt acatatattt tttctattt aaattcatat gagaaataat ttcaaaccaa    4673
caacttaaga aataacaaca atataaagaa atcgttgtaa tgaatacata ctaattattg    4733
cactttctga tatatcgaaa cagtagctca ctgaaagttt accaactatt ataattgcta    4793
tcaagactgc tgaacttatt tgttcgtaga tgtcgatggt tgaaaaaatc ttggccctaa    4853
cagcaataat gtaaaatatt atactcagta atgttcgcta tatgcaaatt ataatagact    4913
caacagtaaa aataatgcat ataatatgta ttaaatgtta actccaaatg cccgtaacat    4973
aaggattcaa attatataat atttatgtaa atgtctttga tacaatggat aactttgtca    5033
attaaaaaaa ttttcatttt gacgaaaaac gaatgaattt agttttaagg tactaagcaa    5093
gcgttaaaat aaactcagat atattatatg aaatattact tcgaatgacg aagttagaaa    5153
tgttgcacaa acattggtgc tattttcatt cgatttttat atttccgcaa attttgaaac    5213 attttgaaa ttaataacat gctcaaatcg tgtataaaat ataggcaatc ctaaaaaata    5273 aacatttat caaacatta caaaaaatac ccagagcata tatatatata tatatatata    5333
tatatatata tatgtatata tatatatgta tgtatatata tatatatata tatatatata    5393
tacatgcatc taaaataata tatagagaaa attgtatgaa aaagggaatg aaccctgaaa    5453
cccctatata ccacaatatt tataagtatt aatatattgt accaaatatt                5503
```

<210> SEQ ID NO 5
<211> LENGTH: 482
<212> TYPE: PRT
<213> ORGANISM: Ctenocephalides felis

<400> SEQUENCE: 5

Met Ala Ala Leu Thr Arg Ala Thr Met Gly Ala Leu Leu Leu Ala Leu
1               5                   10                  15

Ser Pro Ala Leu Leu Leu Ile Trp Leu Pro Tyr Ala Asp Ala Ala Thr
            20                  25                  30

Gly Gly Gly Ser Met Tyr Gly Asp Val Asn Ile Ser Ala Ile Leu Asp
        35                  40                  45

Asn Phe Ser Val Ser Tyr Asp Lys Arg Val Arg Pro Asn Tyr Gly Gly
    50                  55                  60

Pro Pro Val Glu Val Gly Val Thr Met Tyr Val Leu Ser Ile Ser Ser
65                  70                  75                  80

Leu Ser Glu Val Lys Met Asp Phe Thr Leu Asp Phe Tyr Phe Arg Gln
            85                  90                  95

```
Phe Trp Thr Asp Pro Arg Leu Ala Tyr Arg Lys Arg Pro Gly Val Glu
            100                 105                 110

Thr Leu Ser Val Gly Ser Glu Phe Ile Lys Asn Ile Trp Val Pro Asp
        115                 120                 125

Thr Phe Phe Val Asn Glu Lys Gln Ser Tyr Phe His Ile Ala Thr Thr
    130                 135                 140

Ser Asn Glu Phe Ile Arg Ile His His Ser Gly Ser Ile Thr Arg Ser
145                 150                 155                 160

Ile Arg Leu Thr Ile Thr Ala Ser Cys Pro Met Asn Leu Gln Tyr Phe
                165                 170                 175

Pro Met Asp Arg Gln Leu Cys His Ile Glu Ile Glu Ser Phe Gly Tyr
            180                 185                 190

Thr Met Arg Asp Ile Arg Tyr Lys Trp Asn Glu Gly Pro Asn Ser Val
        195                 200                 205

Gly Val Ser Asn Glu Val Ser Leu Pro Gln Phe Lys Val Leu Gly His
    210                 215                 220

Arg Gln Arg Ala Met Glu Ile Ser Leu Thr Thr Gly Asn Tyr Ser Arg
225                 230                 235                 240

Leu Ala Cys Glu Ile Gln Phe Val Arg Ser Met Gly Tyr Tyr Leu Ile
                245                 250                 255

Gln Ile Tyr Ile Pro Ser Gly Leu Ile Val Ile Ile Ser Trp Val Ser
            260                 265                 270

Phe Trp Leu Asn Arg Asn Ala Thr Pro Ala Arg Val Ser Leu Gly Val
        275                 280                 285

Thr Thr Val Leu Thr Met Thr Thr Leu Met Ser Ser Thr Asn Ala Ala
    290                 295                 300

Leu Pro Lys Ile Ser Tyr Val Lys Ser Ile Asp Val Tyr Leu Gly Thr
305                 310                 315                 320

Cys Phe Val Met Val Phe Ala Ser Leu Leu Glu Tyr Ala Thr Val Gly
                325                 330                 335

Tyr Met Ala Lys Arg Ile His Met Arg Lys Gln Arg Phe Met Ala Ile
            340                 345                 350

Gln Lys Ile Ala Glu Gln Lys Lys Leu Gln Ala Glu Gly Gly Gly Pro
        355                 360                 365

Gly Gly Pro Gly Asp His Ser His Ala Pro Lys Gln Thr Val Arg Phe
    370                 375                 380

Lys Val Arg Asp Pro Lys Ala His Ser Lys Gly Gly Thr Leu Glu Asn
385                 390                 395                 400

Thr Ile Asn Gly Gly Arg Gly Gly Ala Ala Ala Asp Glu Glu Ser Ala
                405                 410                 415

Ala Pro Ala Pro Gln His Leu Ile His Pro Gly Lys Asp Ile Asn Lys
            420                 425                 430

Leu Leu Gly Ile Thr Pro Ser Gly Ile Asp Lys Tyr Ser Arg Ile Val
        435                 440                 445

Phe Pro Val Cys Phe Val Cys Phe Asn Leu Met Tyr Trp Ile Met Tyr
    450                 455                 460

Leu His Val Ser Asp Val Val Ala Asp Asp Leu Val Leu Leu Gly Glu
465                 470                 475                 480

Asp Lys

<210> SEQ ID NO 6
<211> LENGTH: 5503
<212> TYPE: DNA
```

<213> ORGANISM: Ctenocephalides felis

<400> SEQUENCE: 6

```
aatatttggt acaatatatt aaatacttata aatattgtgg tatataggg tttcagggtt      60
cattcccttt ttcatacaat tttctctata tattattta gatgcatgta tatatatata      120
tatatatata tatatataca tacatatata tatatacata tatatatata tatatatata     180
tatatatata tatgctctgg gtattttttg taatgttttg ataaaatgtt tattttttag     240
gattgcctat attttataca cgatttgagc atgttattaa tttcaaaaat gtttcaaaat     300
ttgcggaaat ataaaaatcg aatgaaaata gcaccaatgt ttgtgcaaca tttctaactt     360
cgtcattcga agtaatattt catataatat atctgagttt attttaacgc ttgcttagta     420
ccttaaaact aaattcattc gttttctgtc aaaatgaaaa ttttttaat tgacaaagtt      480
atccattgta tcaaagacat ttacataaat attatataat ttgaatcctt atgttacggg     540
catttggagt taacatttaa tacatattat atgcattatt tttactgttg agtctattat     600
aatttgcata tagcgaacat tactgagtat aatattttac attattgctg ttagggccaa     660
gattttttca accatcgaca tctacgaaca aataagttca gcagtcttga tagcaattat     720
aatagttggt aaactttcag tgagctactg tttcgatata tcagaaagtg caataattag     780
tatgtattca ttacaacgat ttctttatat tgttgttatt tcttaagttg ttggtttgaa     840
attatttctc atatgaattt aaaatagaaa aatatatgt aaaattgttc atgattttca     900
ttttatacaa tagcgctttt aatttttttga ttttgttata ttgatgaaac attaaacgat     960
ttgatatttt caagcgtcgc tttgccgatg gttttaatct aattgaatta gaaaatgaat     1020
acaaaaatat agacaaatag ttttgaggaa atgctaatta ttaacaaata aataatgtta    1080
tttattctta aaatatttaa acataacatt attaaccata tcattacgat aaaaatagaa    1140
tgcaaaaata agttgtttaa caatattcta tttgtctata ccataaatgt ttttaagaca    1200
atgaattaat cgtctgcttg aataaaattt aacaaataat tttaattgtt gttttatata    1260
ttacggggta tcaaataaac atttaaata taacgtacct aatatattat tttaatattt    1320
taatatatat ataacaataa gtctatatgt ttatatatca tcaataatcg ttaaacgatt    1380
tcactatcat tttctcattt tatgttaatt cattgttctg tacatgtaat atatattata    1440
tatgttttct ttctgattaa atacattttt ttcataatag ttatataaac ataaaatttt    1500
attggttagt atctaattta agttatgata tagcatattt actaataaat aattttttt    1560
ttaaagtttt tacatatgta aataaaattt caactaaaag caattttgag taaatgcact    1620
ctatcaatat tctgttatct atcaaaacta aatatataat atgaaataat aaaattgcca   1680
atgcgatttt tacaataata cttattttaa aagtaacata aggtatgttt tataatgacc   1740
aaaattagat accttccaag gctacggtgt cataattgta taacacaagt ttttttgcaa   1800
tttgcatata tgctttttata tatttatata tatttactac gaatgttcgt aacgtacgtt    1860
atgtttccta ttactttgtt aacatatgct tgtatatata tgtacttaaa tatctttaac   1920
ctatctttat aattaatatc agtttagaat ttccttgttcg cctcatccga accggcatac   1980
tgggcgtatt ccgaatccgt cgcaatgccg cccagtacgc ccgcccttgc gagactctaa   2040
attatatcat agttttctta gctacgagtc gcatcatcgg atataaatat atagtaaact   2100
ctttatttga agacaaatgg aagaagagat atccattgta ttagtatatt tatcaaacaa   2160
tgatttgaat tctttgatca caatgctttg tatcctatat acacgaaacc atcactaccg   2220
tttctaaaga tagtatagaa cactaaattt cttaaacaag acagtaataa aacgataaca   2280
```

-continued

```
ttttttgtgg accatagaac tattttatgt ggaaccactt agcatgtcgt cgttgtcgaa    2340
gccttaattt ttggtttaaa atatgttcgc attagtgcta atggaaattc atccaattga    2400
atactttgaa tactgggtgt tgaatattat tactcttgtg gctagattga aaaattggaa    2460
gtataaaaac agcattctgt ctactatatt acgttacatg aatgtgcaat tttatttatt    2520
gttgtgtaaa ctaaaattca ttcaaatgta aagtttactc tatttctgag atgcgacttg    2580
acgcgattca ttagtctaag tcaacactgt cgttggcggc ttacggtatc tctatacata    2640
cgaagtgcga taccaggtga caacttatct aatatacgt gtgagtatgt gtgagtgagc    2700
gaattaatgg tacaaatata aaccctacgt gatgcgagat ggaatgattt ctagcccgat    2760
cggccgacaa tttgcttaca cacgtaacga actcatgtgc ttatatttct tgtttggtat    2820
ctgtgatctc tttagtatca tagttatta tgctatatta tatattcata caattaataa    2880
ttggaacggg ttcatacata tataataagg aatgctacat acgggcacga tacacccttt    2940
tcatttatca tttatgcatt tgtgtatata tatatagttt atatagttat atgtcaggaa    3000
taataaaacc gttcagaata tatcaccgat gcctttgttg ctccttttctt ctgtgtcttg    3060 aattatccgt cgcgcaaagt ggagaatgtc cgcatcgagt actcccgtac gggcccaaga    3120
acaaacaagt ggcgatcccg tcacgacaag atgacgcgaa acaaggggg aaacctcgcg    3180 tcacacgctc tatgcaccac ccgcctcggt ccggacaac acacgtgttt agtgcagctg    3240
ctcgctacat cggcaacgtc gcgcgatcga atattttgcg ttttatgtgc ccgacattgt    3300
tttgtctgtc gtctgcctga tctcgttctg gcaattggat catgtcctgc cgatgcaggg    3360
gcgcggagac ccagcgtccc gtcagcccgt acccgagagt cttaaccggg tgccctcagt    3420
ggttcccgcg taacattcga cccgtacgtg gcaagagccg acgctcggc ggttgcgaga    3480 accgcgcttc tcccatgccc aaatgttgca gaagggatat aggtgtataa ttctacaatt    3540
ggatcgaaca taacaggtga aggtttctga tagattaaga ataagtaaaa aaatgatatg    3600
ggatttttta agaaaccata gtgatcaatt acaataggca acggattgag tatgggagtg    3660
catactgggg gcgccctcta tttgtcttct cccaggagca ccaggtcgtc ggccaccacg    3720
tcgctcacgt gcagatacat gatccagtac atcaagttga agcaaacgaa gcagaccggg    3780
aacacgatgc gcgagtactt gtcgatgccc gacgagtga taccgagcag cttgttgatg    3840
tccttgccgg ggtggatgag gtgttggggc gctggcgcgg cgctctcctc gtcggcggcc    3900
gccccgcctc gccccccgtt gattgtgttc tcgagggtgc cgcccttgga atgcgccttc    3960
gggtcgcgaa ccttgaaccg cactgtttgt ttgggcgcat gggaatgatc gccggggcct    4020
cctggcccgc cgccttcagc ttgtagtttc ttttgttctg caattttctg aatcgccatg    4080
aacctctgtt ttctcatatg gatgcgctta gccatgtagc caacagtggc atattctaat    4140
aaactagcga acaccattac gaaacaggtc ccaggtaga cgtctataga tttgacgtat    4200 gatattttg gtagcgcggc gtttgtcgat gacattagag ttgtcatggt caacacagtg    4260
gtcactccga gagagactcg agctggtgta gcattacgat tcagccaaaa cgatacccac    4320
gatatgatca cgataagacc agacggaatg tagatttgga tgaggtagta gcccatagaa    4380
cgcacgaatt gaatctcgca cgccaggcga gaatagtttc ctgttgtgag actgatctcc    4440
attgctcgtt gtcgatgtcc caggactttg aattgcggca gcgacacctc gttagagacc    4500
cccactgagt tcggtccttc gttccactta tatcgaatat cgcgcatcgt gtagccgaag    4560
ctctcgattt ctatgtgaca aagttgtctg tccatagggaa agtattgaag attcattgga    4620
```

-continued

```
catgaggcag tgatcgtcag ccgtatgctc ctcgtgatgg aaccagagtg gtggattcgt      4680
atgaactcgt tgctggtggt tgcgatgtgg aagtaagatt gtttctcgtt tacgaagaat      4740
gtgtcaggga cccatatgtt tttaataaac tcggaaccca cagaaagcgt ttcgacaccg      4800 ggacgttttcc tgtacgctag ccgcggatcc gtccagaatt gccgaaagta aaagtccagc    4860
gtgaagtcca ttttgacttc ggacagcgaa ctgatggaga ggacgtacat cgtgacacca      4920
acttccactg gaggtcctcc ataattcggt cttactcttt tgtcgtagct gacgctgaag      4980
ttatccaaga tggcagaaat gttgacgtcg ccgtacatac tgccgccccc cgtcgcggca      5040
tccgcgtacg gtagccatat cagcaacagg gccggactga gggccagcag gagggccccc      5100
atggttgcgc gagtcagcgc cgccatgccc ccgctacacc agccgcccct ggcgcatctc      5160
accgacggcc cggattcttc atttgggcct cgatgttaca tgtccttgac ggacatttca      5220
cacacaatta ataataatat gataggtgca caccgtgacg acttgatcgt ctggtttatt      5280
tcagtttgca gcaaatttat ttccaacttg ctttataggc gcttgtaata cttatcgaac      5340
aaagttttta aacgaacttt acgtacgcag agctgtcagt gtccaaattt gtcaaaatat      5400
gtctctacaa ttgaaatcaa atcagtacct atcggacgac agaacgcgcg cgtgttcgaa      5460
acagttgaca gttgacgttt gttacgtgtg ccgaaggtgt acg                        5503
```

```
<210> SEQ ID NO 7
<211> LENGTH: 1446
<212> TYPE: DNA
<213> ORGANISM: Ctenocephalides felis

<400> SEQUENCE: 7
```

```
atggcggcgc tgactcgcgc aaccatgggg gccctcctgc tggccctcag tccggccctg       60
ttgctgatat ggctaccgta cgcggatgcc gcgacggggg gcggcagtat gtacggcgac      120
gtcaacattt ctgccatctt ggataacttc agcgtcagct acgacaaaag agtaagaccg      180
aattatggag gacctccagt ggaagttggt gtcacgatgt acgtcctctc catcagttcg      240
ctgtccgaag tcaaaatgga cttcacgctg gactttact ttcggcaatt ctggacggat       300
ccgcggctag cgtacaggaa acgtcccggt gtcgaaacgc tttctgtggg ttccgagttt      360
attaaaaaca tatgggtccc tgacacattc ttcgtaaacg agaaacaatc ttacttccac      420
atcgcaacca ccagcaacga gttcatacga atccaccact ctggttccat cacgaggagc      480
atacggctga cgatcactgc ctcatgtcca atgaatcttc aatacttccc tatggacaga      540
caactttgtc acatagaaat cgagagcttc ggctacacga tgcgcgatat cgatataag       600 tggaacgaag gaccgaactc agtgggggtc tctaacgagg tgtcgctgcc gcaattcaaa      660
gtcctgggac atcgacaacg agcaatggag atcagtctca caacaggaaa ctattctcgc      720
ctggcgtgcg agattcaatt cgtgcgttct atgggctact acctcatcca aatctacatt      780
ccgtctggtc ttatcgtgat catatcgtgg gtatcgtttt ggctgaatcg taatgctaca      840
ccagctcgag tctctctcgg agtgaccact gtgttgacca tgacaactct aatgtcatcg      900
acaaacgccg cgctaccaaa atatcatacg gtcaaatcta tagacgtcta cctgggcacc      960
tgtttcgtaa tggtgttcgc tagtttatta gaatatgcca ctgttggcta catggctaag     1020
cgcatccata tgagaaaaca gaggttcatg gcgattcaga aaattgcaga acaaaagaaa     1080
ctacaagctg aaggcggcgg gccaggaggc cccggcgatc attcccatgc gcccaaacaa     1140
acagtgcggt tcaaggttcg cgacccgaag gcgcattcca agggcggcac cctcgagaac     1200
acaatcaacg gggggcgagg cggggcggcc gccgacgagg agagcgccgc gccagcgccc     1260
```

```
caacacctca tccaccccgg caaggacatc aacaagctgc tcggtatcac tccgtcgggc    1320
atcgacaagt actcgcgcat cgtgttcccg gtctgcttcg tttgcttcaa cttgatgtac    1380
tggatcatgt atctgcacgt gagcgacgtg gtggccgacg acctggtgct cctgggagaa    1440
gacaaa                                                               1446
```

<210> SEQ ID NO 8
<211> LENGTH: 1446
<212> TYPE: DNA
<213> ORGANISM: Ctenocephalides felis

<400> SEQUENCE: 8

```
tttgtcttct cccaggagca ccaggtcgtc ggccaccacg tcgctcacgt gcagatacat      60
gatccagtac atcaagttga agcaaacgaa gcagaccggg aacacgatgc gcgagtactt     120
gtcgatgccc gacggagtga taccgagcag cttgttgatg tccttgccgg ggtggatgag     180
gtgttggggc gctggcgcgg cgctctcctc gtcggcggcc gccccgcctc gcccccgtt     240 gattgtgttc tcgagggtgc cgcccttgga atgcgcctc gggtcgcgaa ccttgaaccg     300
cactgtttgt ttgggcgcat gggaatgatc gccgggcct cctggcccgc cgccttcagc     360
ttgtagtttc ttttgttctg caattttctg aatcgccatg aacctctgtt ttctcatatg    420
gatgcgctta gccatgtagc caacagtggc atattctaat aaactagcga acaccattac    480
gaaacaggtg cccaggtaga cgtctataga tttgacgtat gatattttg gtagcgcggc    540 gtttgtcgat gacattagag ttgtcatggt caacacagtg gtcactccga gagagactcg    600
agctggtgta gcattacgat tcagccaaaa cgatacccac gatatgatca cgataagacc    660
agacggaatg tagatttgga tgaggtagta gcccatagaa cgcacgaatt gaatctcgca    720
cgccaggcga gaatagtttc ctgttgtgag actgatctcc attgctcgtt gtcgatgtcc    780
caggactttg aattgcggca gcgacacctc gttagagacc cccactgagt tcggtccttc    840
gttccactta tatcgaatat cgcgcatcgt gtagccgaag ctctcgattt ctatgtgaca    900
aagttgtctg tccataggga agtattgaag attcattgga catgaggcag tgatcgtcag    960
ccgtatgctc ctcgtgatgg aaccagagtg gtggattcgt atgaactcgt tgctggtggt   1020
tgcgatgtgg aagtaagatt gtttctcgtt tacgaagaat gtgtcaggga cccatatgtt   1080
tttaataaac tcggaaccca cagaaagcgt ttcgacaccg ggacgtttcc tgtacgctag   1140
ccgcggatcc gtccagaatt gccgaaagta aaagtccagc gtgaagtcca ttttgacttc   1200
ggacagcgaa ctgatggaga ggacgtacat cgtgacacca acttccactg gaggtcctcc   1260
ataattcggt cttactcttt tgtcgtagct gacgctgaag ttatccaaga tggcagaaat   1320
gttgacgtcg ccgtacatac tgccgccccc cgtcgcggca tccgcgtacg gtagccatat   1380
cagcaacagg gccggactga gggccagcag gagggccccc atggttgcgc gagtcagcgc   1440
cgccat                                                              1446
```

<210> SEQ ID NO 9
<211> LENGTH: 717
<212> TYPE: DNA
<213> ORGANISM: Ctenocephalides felis
<220> FEATURE:
<221> NAME/KEY: CDS
<222> LOCATION: (1)..(717)

<400> SEQUENCE: 9

```
atg gcg gcg ctg act cgc gca acc atg ggg gcc ctc ctg ctg gcc ctc     48
```

```
Met Ala Ala Leu Thr Arg Ala Thr Met Gly Ala Leu Leu Leu Ala Leu
1               5                   10                  15 agt ccg gcc ctg ttg ctg ata tgg cta ccg tac gcg gat gcc gcg acg     96
Ser Pro Ala Leu Leu Leu Ile Trp Leu Pro Tyr Ala Asp Ala Ala Thr
                20                  25                  30 ggg ggc ggc agt atg tac ggc gac gtc aac att tct gcc atc ttg gat    144
Gly Gly Gly Ser Met Tyr Gly Asp Val Asn Ile Ser Ala Ile Leu Asp
            35                  40                  45 aac ttc agc gtc agc tac gac aaa aga gta aga ccg aat tat gga gga    192
Asn Phe Ser Val Ser Tyr Asp Lys Arg Val Arg Pro Asn Tyr Gly Gly
    50                  55                  60 cct cca gtg gaa gtt ggt gtc acg atg tac gtc ctc tcc atc agt tcg    240
Pro Pro Val Glu Val Gly Val Thr Met Tyr Val Leu Ser Ile Ser Ser
65                  70                  75                  80 ctg tcc gaa gtc aaa atg gac ttc acg ctg gac ttt tac ttt cgg caa    288
Leu Ser Glu Val Lys Met Asp Phe Thr Leu Asp Phe Tyr Phe Arg Gln
                85                  90                  95 ttc tgg acg gat ccg cgg cta gcg tac agg aaa cgt ccc ggt gtc gaa    336
Phe Trp Thr Asp Pro Arg Leu Ala Tyr Arg Lys Arg Pro Gly Val Glu
            100                 105                 110 acg ctt tct gtg ggt tcc gag ttt att aaa aac ata tgg gtc cct gac    384
Thr Leu Ser Val Gly Ser Glu Phe Ile Lys Asn Ile Trp Val Pro Asp
    115                 120                 125 aca ttc ttc gta aac gag aaa caa tct tac ttc cac atc gca acc acc    432
Thr Phe Phe Val Asn Glu Lys Gln Ser Tyr Phe His Ile Ala Thr Thr
130                 135                 140 agc aac gag ttc ata cga atc cac cac tct ggt tcc atc acg agg agc    480
Ser Asn Glu Phe Ile Arg Ile His His Ser Gly Ser Ile Thr Arg Ser
145                 150                 155                 160 ata cgg ctg acg atc act gcc tca tgt cca atg aat ctt caa tac ttc    528
Ile Arg Leu Thr Ile Thr Ala Ser Cys Pro Met Asn Leu Gln Tyr Phe
                165                 170                 175 cct atg gac aga caa ctt tgt cac ata gaa atc gag agc ttc ggc tac    576
Pro Met Asp Arg Gln Leu Cys His Ile Glu Ile Glu Ser Phe Gly Tyr
            180                 185                 190 acg atg cgc gat att cga tat aag tgg aac gaa gga ccg aac tca gtg    624
Thr Met Arg Asp Ile Arg Tyr Lys Trp Asn Glu Gly Pro Asn Ser Val
    195                 200                 205 ggg gtc tct aac gag gtg tcg ctg ccg caa ttc aaa gtc ctg gga cat    672
Gly Val Ser Asn Glu Val Ser Leu Pro Gln Phe Lys Val Leu Gly His
210                 215                 220 cga caa cga gca atg gag atc agt ctc aca aca gga aac tat tct        717
Arg Gln Arg Ala Met Glu Ile Ser Leu Thr Thr Gly Asn Tyr Ser
225                 230                 235

<210> SEQ ID NO 10
<211> LENGTH: 239
<212> TYPE: PRT
<213> ORGANISM: Ctenocephalides felis

<400> SEQUENCE: 10

Met Ala Ala Leu Thr Arg Ala Thr Met Gly Ala Leu Leu Leu Ala Leu
1               5                   10                  15

Ser Pro Ala Leu Leu Leu Ile Trp Leu Pro Tyr Ala Asp Ala Ala Thr
                20                  25                  30

Gly Gly Gly Ser Met Tyr Gly Asp Val Asn Ile Ser Ala Ile Leu Asp
            35                  40                  45

Asn Phe Ser Val Ser Tyr Asp Lys Arg Val Arg Pro Asn Tyr Gly Gly
    50                  55                  60
```

```
Pro Val Glu Val Gly Val Thr Met Tyr Val Leu Ser Ile Ser Ser
 65                  70                  75                  80

Leu Ser Glu Val Lys Met Asp Phe Thr Leu Asp Phe Tyr Phe Arg Gln
                 85                  90                  95

Phe Trp Thr Asp Pro Arg Leu Ala Tyr Arg Lys Arg Pro Gly Val Glu
             100                 105                 110

Thr Leu Ser Val Gly Ser Glu Phe Ile Lys Asn Ile Trp Val Pro Asp
         115                 120                 125

Thr Phe Phe Val Asn Glu Lys Gln Ser Tyr Phe His Ile Ala Thr Thr
     130                 135                 140

Ser Asn Glu Phe Ile Arg Ile His His Ser Gly Ser Ile Thr Arg Ser
145                 150                 155                 160

Ile Arg Leu Thr Ile Thr Ala Ser Cys Pro Met Asn Leu Gln Tyr Phe
                165                 170                 175

Pro Met Asp Arg Gln Leu Cys His Ile Glu Ile Glu Ser Phe Gly Tyr
            180                 185                 190

Thr Met Arg Asp Ile Arg Tyr Lys Trp Asn Glu Gly Pro Asn Ser Val
        195                 200                 205

Gly Val Ser Asn Glu Val Ser Leu Pro Gln Phe Lys Val Leu Gly His
    210                 215                 220

Arg Gln Arg Ala Met Glu Ile Ser Leu Thr Thr Gly Asn Tyr Ser
225                 230                 235

<210> SEQ ID NO 11
<211> LENGTH: 717
<212> TYPE: DNA
<213> ORGANISM: Ctenocephalides felis

<400> SEQUENCE: 11
agaatagttt cctgttgtga gactgatctc cattgctcgt tgtcgatgtc ccaggacttt      60
gaattgcggc agcgacacct cgttagagac ccccactgag ttcggtcctt cgttccactt     120
atatcgaata tcgcgcatcg tgtagccgaa gctctcgatt tctatgtgac aaagttgtct     180
gtccataggg aagtattgaa gattcattgg acatgaggca gtgatcgtca gccgtatgct     240
cctcgtgatg gaaccagagt ggtggattcg tatgaactcg ttgctggtgg ttgcgatgtg     300
gaagtaagat tgtttctcgt ttacgaagaa tgtgtcaggg acccatatgt ttttaataaa     360
ctcggaaccc acagaaagcg tttcgacacc gggacgtttc ctgtacgcta gccgcggatc     420
cgtccagaat tgccgaaagt aaaagtccag cgtgaagtcc attttgactt cggacagcga     480
actgatggag aggacgtaca tcgtgacacc aacttccact ggaggtcctc cataattcgg     540
tcttactctt ttgtcgtagc tgacgctgaa gttatccaag atggcagaaa tgttgacgtc     600
gccgtacata ctgccgcccc cgtcgcggc atccgcgtac ggtagccata tcagcaacag      660
ggccggactg agggccagca ggagggcccc catggttgcg cgagtcagcg ccgccat        717

<210> SEQ ID NO 12
<211> LENGTH: 24
<212> TYPE: DNA
<213> ORGANISM: Artificial
<220> FEATURE:
<223> OTHER INFORMATION: Synthetic Primer

<400> SEQUENCE: 12
atggatttya caytggaytt ytay                                             24

<210> SEQ ID NO 13
```

```
<211> LENGTH: 20
<212> TYPE: DNA
<213> ORGANISM: Artificial
<220> FEATURE:
<223> OTHER INFORMATION: Synthetic Primer

<400> SEQUENCE: 13
taatacgact cactataggg                                               20

<210> SEQ ID NO 14
<211> LENGTH: 21
<212> TYPE: DNA
<213> ORGANISM: Artificial
<220> FEATURE:
<223> OTHER INFORMATION: Synthetic Primer
<220> FEATURE:
<221> NAME/KEY: misc_feature
<222> LOCATION: (4)..(4)
<223> OTHER INFORMATION: n = unknown

<400> SEQUENCE: 14
attnakccar aatgawaccc a                                             21

<210> SEQ ID NO 15
<211> LENGTH: 21
<212> TYPE: DNA
<213> ORGANISM: Artificial
<220> FEATURE:
<223> OTHER INFORMATION: Synthetic Primer

<400> SEQUENCE: 15
aaacatatgg gtccctgaca c                                             21

<210> SEQ ID NO 16
<211> LENGTH: 20
<212> TYPE: DNA
<213> ORGANISM: Artificial
<220> FEATURE:
<223> OTHER INFORMATION: Synthetic Primer

<400> SEQUENCE: 16
tatcgcgcat cgtgtagccg                                               20

<210> SEQ ID NO 17
<211> LENGTH: 28
<212> TYPE: DNA
<213> ORGANISM: Artificial
<220> FEATURE:
<223> OTHER INFORMATION: Synthetic Primer

<400> SEQUENCE: 17
gggctcgagc atggcggcgc tgactcgc                                      28

<210> SEQ ID NO 18
<211> LENGTH: 37
<212> TYPE: DNA
<213> ORGANISM: Artificial
<220> FEATURE:
<223> OTHER INFORMATION: Synthetic Primer

<400> SEQUENCE: 18
attgaattct tagggagaat agtttcctgt tgtgaga                            37

<210> SEQ ID NO 19
<211> LENGTH: 23
<212> TYPE: DNA
<213> ORGANISM: Artificial
```

-continued

```
<220> FEATURE:
<223> OTHER INFORMATION: Synthetic Primer

<400> SEQUENCE: 19
tataaactag cgaacaacat tac                                              23

<210> SEQ ID NO 20
<211> LENGTH: 22
<212> TYPE: DNA
<213> ORGANISM: Artificial
<220> FEATURE:
<223> OTHER INFORMATION: Synthetic Primer

<400> SEQUENCE: 20
gattcaattc gtgcgttcta tg                                               22
```

FLEA GABA RECEPTOR SUBUNIT NUCLEIC ACID MOLECULES

FIELD OF THE INVENTION

The present invention relates to flea GABA receptor subunit nucleic acid molecules, proteins encoded by such nucleic acid molecules, antibodies raised against such proteins, and inhibitors of such proteins. The present invention also includes methods to obtain such proteins, nucleic acid molecules, antibodies, and inhibitory compounds. The present invention also includes therapeutic compositions comprising such inhibitors, as well as uses thereof.

BACKGROUND OF THE INVENTION

Flea infestation of animals is a health and economic concern for pet owners. In particular, the bites of fleas are a problem for animals maintained as pets because the infestation becomes a source of annoyance not only for the pet but also for the pet owner who may find his or her home generally contaminated with insects. Fleas are known to directly cause a variety of diseases, including allergy, and also carry a variety of infectious agents including, but not limited to, endoparasites (e.g., nematodes, cestodes, trematodes and protozoa), bacteria and viruses. As such, fleas are a problem not only when they are on an animal but also when they are in the general environment of the animal.

The medical importance of flea infestation has prompted the development of reagents capable of controlling flea infestation. Commonly encountered methods to control flea infestation are generally focused on use of insecticides, which are often unsuccessful for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide.

Gamma-aminobutyric acid (GABA) is a major neurotransmitter in both insects and vertebrates bound by GABA receptors, which are intrinsic membrane glycoproteins in vertebrate and invertebrate neuronal tissues that are members of the ligand-gated ion channel superfamily of receptors. Researchers have isolated three insect clones encoding putative GABA receptors from *Drosophila melanogaster*, (1) Rdl (resistance to dieldrin), (2) Grd (GABA and glycine-like receptor of *Drosophila*); and (3) Lcch3 (ligand-gated chloride channel homologue 3). Insect GABA receptor is a known target of various insecticides including cyclodienes such as dieldrin, and phenylpyrazoles such as fipronil; see for example Casida, J. E., 1993, *Archives of Insect Biochem. and Physiol.* 22:13-23, and Cole et al., 1993, Pesticide Biochem. and Physiol., 46:47-54. In several insects, including Drosophila, beetles, mosquito, whitefly, cockroach and aphids, resistance to cyclodienes has been linked to a single amino acid mutation from alanine to serine.

Prior investigations have described certain insect GABA receptor subunit protein and/or nucleic acid sequences, including for example, ffrench-Constant et al. 1991, *Proc. Nat. Acad. Sci.* 88:7209-7213, as well certain vertebrate protein and/or nucleic acid sequences, including for example, Pritchett et al. 1989, Nature, 338:582-585. Unfortunately, many insecticides that target GABA receptors also act on the $GABA_A$ receptors of mammals, therefore creating difficulties in using the GABA receptor as a target to kill fleas. Due to the necessity of limiting potential cross-reactivity against the GABA receptors of the animal to be treated, it would be a distinct advantage to have the sequence of the flea GABA receptor, in order to create treatments which are efficacious against fleas while minimizing toxicity to the host animal.

Therefore, isolation and sequencing of flea GABA receptor subunit genes may be critical for use in identifying specific agents for treating animals for flea infestation.

SUMMARY OF THE INVENTION

The present invention provides flea GABA receptor subunit proteins; nucleic acid molecules encoding flea GABA receptor subunit proteins; antibodies raised against such proteins (i.e., anti-flea GABA receptor subunit antibodies); mimetopes of such proteins or antibodies; and compounds that inhibit flea GABA receptor subunit activity (i.e. inhibitory compounds or inhibitors).

The present invention also includes methods to obtain such proteins, mimetopes, nucleic acid molecules, antibodies and inhibitory compounds. The present invention also includes the use of proteins and antibodies to identify such inhibitory compounds as well as assay kits to identify such inhibitory compounds. Also included in the present invention are therapeutic compositions comprising proteins, mimetopes, nucleic acid molecules, antibodies and inhibitory compounds of the present invention including therapeutic compounds derived from a protein of the present invention that inhibit the activity of flea GABA receptor subunit proteins; also included are uses of such therapeutic compounds.

One embodiment of the present invention is an isolated flea GABA receptor subunit nucleic acid molecule that hybridizes with a nucleic acid sequence having SEQ ID NO:1, SEQ ID NO:3; SEQ ID NO:4, SEQ ID NO:6, SEQ ID NO:7, SEQ ID NO:8, SEQ ID NO:9, and/or SEQ ID NO:11, under conditions that allow less than or equal to 20% base pair mismatch. Another embodiment of the present invention is an isolated flea GABA receptor subunit nucleic acid molecule having a nucleic acid sequence that is at least 80% identical to SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11, or fragments thereof at least about 35 nucleotides in length.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

Another embodiment of the present invention includes an isolated flea GABA receptor subunit protein that is at least 95% identical to an amino acid sequence selected from the group consisting of SEQ ID NO:2, SEQ ID NO:5, and/or SEQ ID NO:10 and fragments thereof, wherein such fragments can elicit an immune response against respective flea GABA receptor subunit proteins or have activity comparable to respective flea GABA receptor subunit proteins.

Another embodiment of the present invention includes an isolated flea GABA receptor subunit protein encoded by a nucleic acid molecule that hybridizes with a nucleic acid sequence having SEQ ID NO:3, SEQ ID NO:8, and/or SEQ ID NO:11, under conditions that allow less than or equal to 20% base pair mismatch.

Another embodiment of the present invention includes a composition comprising an excipient and a compound selected from the group consisting of nucleic acid molecules, proteins, and antibodies of the present invention and a method to treat an animal for flea infestation comprising administering such a composition to such an animal.

Another embodiment of the present invention includes a method to detect an inhibitor of flea GABA receptor subunit activity, said method comprising (a) contacting an isolated flea GABA receptor subunit protein of the present invention, with a putative inhibitory compound under conditions in which, in the absence of said compound, said protein has flea GABA receptor subunit protein activity, and (b) determining if said putative inhibitory compound inhibits flea GABA receptor subunit protein activity.

DETAILED DESCRIPTION OF THE INVENTION

The present invention provides for flea GABA receptor subunit nucleic acid molecules, proteins encoded by such nucleic acid molecules, antibodies raised against such proteins, and inhibitors of such proteins. As used herein, flea GABA receptor subunit nucleic acid molecules and proteins encoded by such nucleic acid molecules are also referred to as GABA receptor subunit nucleic acid molecules and proteins of the present invention, respectively. Flea GABA receptor subunit nucleic acid molecules and proteins of the present invention can be isolated from a flea or prepared recombinantly or synthetically. Flea GABA receptor subunit nucleic acid molecules of the present invention can be RNA or DNA, or modified forms thereof, and can be double-stranded or single-stranded; examples of nucleic acid molecules include, but are not limited to, complementary DNA (cDNA) molecules, genomic DNA molecules, synthetic DNA molecules, DNA molecules which are specific tags for messenger RNA, and corresponding mRNA molecules. As such, a flea nucleic acid molecule of the present invention is not intended refer to an entire chromosome within which such a nucleic acid molecule is contained, however, a flea GABA receptor subunit cDNA of the present invention may include all regions such as regulatory regions that control production of flea GABA receptor subunit proteins encoded by such a cDNA (such as, but not limited to, transcription, translation or post-translation control regions) as well as the coding region itself, and any introns or non-translated coding regions. As used herein, the phrase "flea GABA receptor subunit protein" refers to a protein encoded by a flea GABA receptor subunit nucleic acid molecule.

Flea GABA receptor subunit nucleic acid molecules of known length isolated from a flea, such as *Ctenocephalides felis* are denoted "nCfGR$_\#$", for example nCfGR$_{5503}$, wherein "#" refers to the number of nucleotides in that molecule, and flea GABA receptor subunit proteins of known length are denoted "PCfGR$_\#$" (for example PCfGR$_{482}$) wherein "#" refers to the number of amino acid residues in that molecule.

The present invention also provides for flea GABA receptor subunit DNA molecules that are specific tags for messenger RNA molecules. Such DNA molecules can correspond to an entire or partial sequence of a messenger RNA, and therefore, a DNA molecule corresponding to such a messenger RNA molecule (i.e. a cDNA molecule), can encode a full-length or partial-length protein. A nucleic acid molecule encoding a partial-length protein can be used directly as a probe or indirectly to generate primers to identify and/or isolate a cDNA nucleic acid molecule encoding a corresponding, or structurally related, full-length protein. Such a partial cDNA nucleic acid molecule can also be used in a similar manner to identify a genomic nucleic acid molecule, such as a nucleic acid molecule that contains the complete gene including regulatory regions, exons and introns. Methods for using partial flea GABA receptor subunit cDNA molecules and sequences to isolate full-length and corresponding cDNA molecules are described in the examples herein below.

The proteins and nucleic acid molecules of the present invention can be obtained from their natural source, or can be produced using, for example, recombinant nucleic acid technology or chemical synthesis. Also included in the present invention is the use of these proteins and nucleic acid molecules as well as antibodies and inhibitory compounds thereto as therapeutic compositions, as well as in other applications, such as those disclosed below.

One embodiment of the present invention is an isolated protein that includes a flea GABA receptor subunit protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from a natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, isolated flea GABA receptor subunit proteins of the present invention can be full-length proteins or any homologue of such proteins. An isolated protein of the present invention, including a homologue, can be identified in a straight-forward manner by the protein's ability to elicit an immune response against a flea GABA receptor subunit protein or by the protein's ability to exhibit flea GABA receptor subunit activity, e.g. the ability to bind to GABA. Examples of flea GABA receptor subunit homologue proteins include flea GABA receptor subunit proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a flea GABA receptor subunit protein, and/or of binding to an antibody directed against a flea GABA receptor subunit protein. That is, when the homologue is administered to an animal as an immunogen, using techniques known to those skilled in the art, the animal will produce an immune response against at least one epitope of a natural flea GABA receptor subunit protein. The ability of a protein to effect an immune response can be measured using techniques known to those skilled in the art. As used herein, the term "epitope" refers to the smallest portion of a protein or other antigen capable of selectively binding to the antigen binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least 4 amino acids, at least 5 amino acids, at least 6 amino acids, at least 10 amino acids, at least 15 amino acids, at least 20 amino acids, at least 25 amino acids, at least 30 amino acids, at least 35 amino acids, at least 40 amino acids or at least 50 amino acids in length.

In one embodiment of the present invention a flea GABA receptor subunit homologue protein has flea GABA receptor subunit activity, i.e. the homologue exhibits an activity similar to its natural counterpart, e.g. the ability to bind GABA. Methods to detect and measure such activities are known to those skilled in the art.

Flea GABA receptor subunit homologue proteins can be the result of natural allelic variation or natural mutation. Flea GABA receptor subunit protein homologues of the present invention can also be produced using techniques known in the art including, but not limited to, direct modifications to the protein or modifications to the gene encoding the protein using, for example, classic or recombinant DNA techniques to effect random or targeted mutagenesis.

Flea GABA receptor subunit proteins of the present invention are encoded by flea GABA receptor subunit nucleic acid molecules. As used herein, flea GABA receptor subunit nucleic acid molecules include nucleic acid sequences related to natural flea GABA receptor subunit genes, and, preferably, to $C.\ felis$ flea GABA receptor subunit genes. As used herein, flea GABA receptor subunit genes include all regions such as regulatory regions that control production of flea GABA receptor subunit proteins encoded by such genes (such as, but not limited to, transcription, translation or post-translation control regions) as well as the coding region itself, and any introns or non-translated coding regions. As used herein, a nucleic acid molecule that "includes" or "comprises" a sequence may include that sequence in one contiguous array, or may include the sequence as fragmented exons such as is often found for a flea gene. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a $C.\ felis$ flea GABA receptor subunit gene that includes the nucleic acid sequence SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11 either in a consecutive array or interrupted by naturally occurring introns. These nucleic acid sequences are further described herein. For example, nucleic acid sequence SEQ ID NO:7 represents the deduced sequence of the coding strand of a $C.\ felis$ cDNA denoted herein as $C.\ felis$ GABA receptor subunit nucleic acid molecule $nCfGR_{1446}$, the production of which is disclosed in the Examples. Nucleic acid molecule SEQ ID NO:7 comprises an apparently full-length coding region. The complement of SEQ ID NO:7 (represented herein by SEQ ID NO:8) refers to the nucleic acid sequence of the strand fully complementary to the strand having SEQ ID NO:7, which can easily be determined by those skilled in the art. Likewise, a nucleic acid sequence complement of any nucleic acid sequence of the present invention refers to the nucleic acid sequence of the nucleic acid strand that is fully complementary to (i.e., can form a complete double helix with) the strand for which the sequence is cited. It should be noted that since nucleic acid sequencing technology is not entirely error-free, SEQ ID NO:7 (as well as other nucleic acid and protein sequences presented herein) represents an apparent nucleic acid sequence of the nucleic acid molecule encoding a flea GABA receptor subunit protein of the present invention.

Translation of SEQ ID NO:4, the coding strand of $nCfGR_{5503}$, as well as translation of SEQ ID NO:7, the coding strand of $nCfGR_{1446}$, which represents the coding region of $nCfGR_{5503}$, yields a protein of 482 amino acids, denoted herein as $PCfGR_{482}$, the amino acid sequence of which is presented in SEQ ID NO:5, assuming an (a) initiation codon extending from nucleotide 378-380 of SEQ ID NO:4, or from nucleotide 1to nucleotide 3 of SEQ ID NO:7, respectively; and (b) a termination codon extending from nucleotide 1824 to 1826 of SEQ ID NO:4.

In one embodiment, a gene or other nucleic acid molecule of the present invention can be an allelic variant that includes a similar but not identical sequence to SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11 For example, an allelic variant of a $C.\ felis$ GABA receptor subunit gene including SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11 is a gene that occurs at essentially the same locus (or loci) in the genome as the gene including SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given flea species, since the genome is diploid, and sexual reproduction will result in the reassortment of alleles.

In one embodiment of the present invention, isolated flea GABA receptor subunit proteins are encoded by nucleic acid molecules that hybridize under stringent hybridization conditions to genes or other nucleic acid molecules encoding flea GABA receptor subunit proteins, respectively. The minimal size of flea GABA receptor subunit proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the flea GABA receptor subunit nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a flea GABA receptor subunit protein is at least about 12 to about 15 nucleotides in length if the nucleic acid molecule is GC-rich and at least about 15 to about 17 bases in length if it is AT-rich. The minimal size of a nucleic acid molecule used to encode a flea GABA receptor subunit protein homologue of the present invention is from about 12 to about 18 nucleotides in length. Thus, the minimal size of flea GABA receptor subunit protein homologues of the present invention is from about 4 to about 6 amino acids in length. There is no limit, other than a practical limit, on the maximal size of a nucleic acid molecule encoding a flea GABA receptor subunit protein of the present invention because a nucleic acid molecule of the present invention can include a portion of a gene or cDNA or RNA, an entire gene or cDNA or RNA, or multiple genes or cDNA or RNA. The preferred size of a protein encoded by a nucleic acid molecule of the present invention depends on whether a full-length, fusion, multivalent, or functional portion of such a protein is desired.

Stringent hybridization conditions are determined based on defined physical properties of the flea GABA receptor subunit nucleic acid molecule to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5°\ C. + 16.6 \log M + 0.41(\%\ G+C) - 500/n - 0.61(\%\ \text{formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with greater than a specified % base pair mismatch will hybridize. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a flea GABA receptor subunit nucleic acid molecule of about 150 bp in length or greater, the following conditions could preferably be used. The average G+C content of flea DNA is about 37%, as calculated from known flea nucleic acid sequences. The unknown nucleic acid molecules would be attached to a support membrane, and the 150 bp probe would be labeled, e.g. with a radioactive tag. The hybridization reaction could be carried out in a solution comprising 2×SSC in the absence of nucleic acid helix destabilizing compounds, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, in a wash solution comprising 1×SSC in the absence of nucleic acid helix destabilizing compounds, the $T_m$ of perfect hybrids would be about 79.6° C.:

$$81.5°\ C. + 16.6 \log(0.15M) + (0.41 \times 37) - (500/150) - (0.61 \times 0) = 79.6°\ C.$$

Thus, to achieve hybridization with nucleic acid molecules having about 20% base pair mismatch, hybridization washes would be carried out at a temperature of less than or equal to 59.6° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 20% base pair mismatch will not vary significantly from 59.6° C. Similarly, to achieve hybridization with nucleic acid molecules having about 10% base pair mismatch, hybridization washes would be carried out at a temperature of less than or equal to 69.6° C. and to achieve hybridization with nucleic acid molecules having about 5% base pair mismatch, hybridization washes would be carried out at a temperature of less than or equal to 74.6° C.

Furthermore, it is known in the art that there are commercially available computer programs for determining the degree of similarity between two nucleic acid or protein sequences. These computer programs include various known methods to determine the percentage identity and the number and length of gaps between hybrid nucleic acid molecules or proteins. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the SEQLAB® WISCONSIN PACKAGE™ Version 10.0-UNIX sequence analysis software, available from Genetics Computer Group, Madison, Wis. (hereinafter "SEQLAB® sequence analysis software"); and DNASIS® sequence analysis software, version 2.0, available from Hitachi Software, San Bruno, Calif. (hereinafter "DNASIS® sequence analysis software"). Such software programs represent a collection of algorithms paired with a graphical user interface for using the algorithms. The DNASIS® sequence analysis software and SEQLAB® sequence analysis software software, for example, employ a particular algorithm, the Needleman-Wunsch algorithm to perform pair-wise comparisons between two sequences to yield a percentage identity score, see Needleman, S. B. and Wunsch, C. D., 1970, *J. Mol. Biol.*, 48, 443, which is incorporated herein by reference in its entirety. Such algorithms, including the Needleman-Wunsch algorithm, are commonly used by those skilled in the nucleic acid and amino acid sequencing art to compare sequences. A preferred method to determine percent identity among amino acid sequences and also among nucleic acid sequences includes using the Needleman-Wunsch algorithm, available in the SEQLAB® sequence analysis software, using the Pairwise Comparison/Gap function with the nwsgapdna.cmp scoring matrix, the gap creation penalty and the gap extension penalties set at default values, and the gap shift limits set at maximum (hereinafter referred to as "default parameters"). An additional preferred method to determine percent identity among amino acid sequences and also among nucleic acid sequences includes using the Higgins-Shay algorithm, available in the DNASIS® sequence analysis software, with the gap penalty set at 5, the number of top diagonals set at 5, the fixed gap penalty set at 10, the k-tuple set at 2, the window size set at 5, and the floating gap penalty set at 10. A particularly preferred method to determine percent identity among amino acid sequences and also among nucleic acid sequences includes using the Needleman-Wunsch algorithm available in the SEQLAB® sequence analysis software, using default parameters.

One embodiment of the present invention includes a flea GABA receptor subunit protein. A preferred flea GABA receptor subunit protein includes a protein encoded by a nucleic acid molecule that hybridizes under conditions that preferably allow less than or equal to 20% base pair mismatch, preferably under conditions that allow less than or equal to 10% base pair mismatch, preferably under conditions that allow less than or equal to 8% base pair mismatch, preferably under conditions that allow less than or equal to 5% base pair mismatch or preferably under conditions that allow less than or equal to 2% base pair mismatch with a nucleic acid molecule selected from the group consisting of SEQ ID NO:3, SEQ ID NO:8, and/or SEQ ID NO:11

Another embodiment of the present invention includes a flea GABA receptor subunit protein encoded by a nucleic acid molecule that hybridizes under conditions comprising, (a) hybridizing in a solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 69.6° C., to an isolated nucleic acid molecule selected from the group consisting of SEQ ID NO:3, SEQ ID NO:6, SEQ ID NO:8, and/or SEQ ID NO:11.

Another preferred flea GABA receptor subunit protein of the present invention includes a protein that is encoded by a nucleic acid molecule that is preferably at least 80% identical, preferably at least 90% identical, preferably at least 92% identical, preferably at least 95% identical or preferably at least 98% identical to a nucleic acid molecule having the nucleic acid sequence SEQ ID NO:1, SEQ ID NO:4, SEQ ID NO:7, and/or SEQ ID NO:9; also preferred are fragments (i.e. portions) of such proteins encoded by nucleic acid molecules that are at least 35 nucleotides. Percent identity as used herein is determined using the Needleman-Wunsch algorithm, available in the SeqLab software using default parameters.

Additional preferred flea GABA receptor subunit proteins of the present invention include proteins having the amino acid sequence SEQ ID NO:2, SEQ ID NO:5, and/or SEQ ID NO:10, and proteins comprising homologues of a protein having the amino acid sequence SEQ ID NO:2, SEQ ID NO:5, and/or SEQ ID NO:10, wherein such a homologue comprises at least one epitope that elicits an immune response against a protein having an amino acid sequence SEQ ID NO:2, SEQ ID NO:5, and/or SEQ ID NO:10. Likewise, also preferred are proteins encoded by nucleic acid molecules comprising nucleic acid sequence SEQ ID NO:1, SEQ ID NO:4, SEQ ID NO:7, and/or SEQ ID NO:9, or by homologues thereof.

A preferred isolated flea GABA receptor subunit protein of the present invention is a protein encoded by at least one of the following nucleic acid molecules: nCfGR$_{183}$, nCfGR$_{5503}$, nCfGR$_{1446}$, and/or nCfGR$_{717}$, or allelic variants of any of these nucleic acid molecules. Also preferred is an isolated protein encoded by a nucleic acid molecule having nucleic acid sequence SEQ ID NO:1, SEQ ID NO:4, SEQ ID NO:7, and/or SEQ ID NO:9; or a protein encoded by an allelic variant of any of these listed nucleic acid molecules.

Preferred proteins of the present invention include proteins that are at least 90%, preferably 92%, preferably 95%, preferably 98%, preferably 99% or preferably 100% identical to PCfGR$_{60}$, PCfGR$_{482}$, PCfGR$_{239}$. Additionally preferred are proteins encoded by allelic variants of a nucleic acid molecules encoding proteins PCfGR$_{60}$, PCfGR$_{482}$, PCfGR$_{239}$. Also preferred are fragments thereof having at least 180 amino acid residues.

Preferred flea GABA receptor subunit proteins of the present invention include proteins having amino acid sequences that are at least 90%, preferably 92%, preferably 95%, preferably at least 98%, preferably at least 99%, or preferably 100% identical to amino acid sequence SEQ ID NO:2, SEQ ID NO:5, and/or SEQ ID NO:10; and proteins encoded by allelic variants of nucleic acid molecules encoding flea GABA receptor subunit proteins having amino acid sequences SEQ ID NO:2, SEQ ID NO:5, and/or SEQ ID NO:10. Also preferred are fragments thereof having at least 180 amino acid residues.

Preferred flea GABA receptor subunit proteins of the present invention include proteins selected from the group consisting of (a) a protein comprising an amino acid sequence selected from the group consisting of SEQ ID NO:2, SEQ ID NO:5, and SEQ ID NO:10; and (b) a protein comprising an at least 180 contiguous amino acid portion identical in sequence to an at least 180 contiguous amino acid portion of an amino acid sequence of (a).

In one embodiment of the present invention, *C. felis* GABA receptor subunit proteins comprise amino acid sequence SEQ ID NO:2, SEQ ID NO:5, and/or SEQ ID NO:10 (including, but not limited to, the proteins consisting of amino acid sequence SEQ ID NO:2, SEQ ID NO:5, and/or SEQ ID NO:10, fusion proteins and multivalent proteins), and proteins encoded by allelic variants of nucleic acid molecules encoding proteins having amino acid sequence SEQ ID NO:2, SEQ ID NO:5, and/or SEQ ID NO:10.

In one embodiment, a preferred flea GABA receptor subunit protein comprises an amino acid sequence of at least 35 amino acids, preferably at least 50 amino acids, preferably at least 100 amino acids, preferably at least 125 amino acids, preferably at least 150 amino acids, preferably at least 175 amino acids, preferably at least 180 amino acids, preferably at least 190 amino acids, preferably at least 200 amino acids, preferably at least 225 amino acids, preferably at least 250 amino acids, preferably at least 275 amino acids, preferably at least 300 amino acids, preferably at least 350 amino acids, preferably at least 400 amino acids, preferably at least 450 amino acids, preferably at least 475 amino acids, preferably at least 480 amino acids, or preferably at least 485 amino acids. In another embodiment, preferred flea GABA receptor subunit proteins comprise full-length proteins, i.e., proteins encoded by full-length coding regions, or post-translationally modified proteins thereof, such as mature proteins from which initiating methionine and/or signal sequences or "pro" sequences have been removed.

Additional preferred flea GABA receptor subunit proteins of the present invention include proteins encoded by nucleic acid molecules comprising at least a portion of $nCfGR_{183}$, $nCfGR_{5503}$, $nCfGR_{1446}$, $nCfGR_{717}$, as well as flea GABA receptor subunit proteins encoded by allelic variants of such nucleic acid molecules. A portion of such a flea GABA receptor subunit nucleic acid molecule is preferably at least 35 nucleotides in length.

Also preferred are flea GABA receptor subunit proteins encoded by nucleic acid molecules having nucleic acid sequences comprising at least a portion of SEQ ID NO:1, SEQ ID NO:4, SEQ ID NO:7, and/or SEQ ID NO:9, as well as allelic variants of these nucleic acid molecules. A portion of such flea GABA receptor subunit nucleic acid molecule is preferably at least 35 nucleotides in length.

In another embodiment, a preferred flea GABA receptor subunit protein of the present invention is encoded by a nucleic acid molecule comprising at least 30 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 450 nucleotides, preferably at least 550 nucleotides, preferably at least 650 nucleotides, preferably at least 750 nucleotides, preferably at least 1000 nucleotides, preferably at least 1500 nucleotides, preferably at least 1750 nucleotides, preferably at least 2000 nucleotides, preferably at least 2250 nucleotides, preferably at least 2500 nucleotides, preferably at least 2750 nucleotides preferably at least 3000 nucleotides, preferably at least 3500 nucleotides, preferably at least 4000 nucleotides, preferably at least 4500 nucleotides, preferably at least 5000 nucleotides or preferably at least 5500 nucleotides in length. Within this embodiment is a flea GABA receptor subunit protein encoded by at least a portion of $nCfGR_{183}$, $nCfGR_{5503}$, $nCfGR_{1446}$, $nCfGR_{717}$, or by an allelic variant of any of these nucleic acid molecules. Preferred flea GABA receptor subunit proteins of the present invention are encoded by nucleic acid molecules comprising apparently full-length flea GABA receptor subunit coding region, i.e., nucleic acid molecules encoding an apparently fullength flea GABA receptor subunit protein, or extracellular domain.

Preferred flea GABA receptor subunit proteins of the present invention can be used to develop inhibitors that, when administered to an animal in an effective manner, are capable of protecting that animal from flea infestation. In accordance with the present invention, the ability of an inhibitor of the present invention to protect an animal from flea infestation refers to the ability of that protein to, for example, treat, ameliorate and/or prevent infestation caused by fleas. In particular, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment of the animal. Such an environment can include not only adult fleas, but also flea eggs and/or flea larvae. The environment can be of any size such that fleas in the environment are able to jump onto and off of a host animal. For example, the environment of an animal can include plants, such as crops, from which fleas infest an animal. As such, it is desirable not only to reduce the flea burden on an animal per se, but also to reduce the flea burden in the environment of the animal.

Suitable fleas to target include any flea that is essentially incapable of causing disease in an animal administered an inhibitor of the present invention. As such, fleas to target include any flea that produces a protein that can be targeted by an inhibitory compound that inhibits a flea flea GABA receptor subunit protein function, thereby resulting in the decreased ability of the parasite to cause disease in an animal. Preferred fleas to target include fleas of the following genera: *Ctenocephalides, Cyopsyllus, Diamanus (Oropsylla), Echidnophaga, Nosopsyllus, Pulex, Tunga*, and *Xenopsylla*, with those of the species *Ctenocephalides canis, Ctenocephalides-felis, Diamanus montanus, Echidnophaga gallinacea, Nosopsyllus faciatus, Pulex irritans, Pulex simulans, Tunga penetrans* and *Xenopsylla cheopis* being more preferred, with *C. felis* being even more preferred. Such fleas are also preferred for the isolation of proteins or nucleic acid molecules of the present invention.

One embodiment of a flea GABA receptor subunit protein of the present invention is a fusion protein that includes a flea GABA receptor subunit protein-containing domain attached to one or more fusion segments. Suitable fusion segments for use with the present invention include, but are not limited to, segments that can: enhance a protein's stability; act as an immunopotentiator; and/or assist in purification of a flea GABA receptor subunit protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the flea GABA receptor subunit-containing domain of the protein and can be susceptible to cleavage in order to enable straight-forward recovery of a flea GABA receptor subunit protein. Fusion proteins are preferably produced by culturing a recombinant cell transformed with a fusion nucleic acid molecule that encodes a protein including the fusion segment attached to either the carboxyl and/or amino terminal end of a flea GABA receptor subunit-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

The present invention also includes mimetopes of flea GABA receptor subunit proteins of the present invention. As used herein, a mimetope of a flea GABA receptor subunit protein of the present invention refers to any compound that is able to mimic the activity of such a flea GABA receptor subunit protein, often because the mimetope has a structure that mimics the particular flea GABA receptor subunit protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a flea GABA receptor subunit nucleic acid molecule, i.e. a nucleic acid molecule that can be isolated from a flea cDNA library. The identifying characteristics of such nucleic acid molecules are heretofore described. A nucleic acid molecule of the present invention can include an isolated natural flea GABA receptor subunit gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a flea GABA receptor subunit nucleic acid molecule of the present invention is from 12 to 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated flea GABA receptor subunit nucleic acid molecules of the present invention, or homologues thereof, can be isolated from a natural source or produced using recombinant DNA technology (e.g., polymerase chain reaction (PCR) amplification or cloning) or chemical synthesis. Isolated flea GABA receptor subunit nucleic acid molecules, and homologues thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a flea GABA receptor subunit protein of the present invention.

A flea GABA receptor subunit nucleic acid molecule homologue can be produced using a number of methods known to those skilled in the art, see, for example, Sambrook et al., ibid., which is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologues can be selected by hybridization with flea GABA receptor subunit nucleic acid molecules or by screening the function of a protein encoded by the nucleic acid molecule (e.g., ability to elicit an immune response against at least one epitope of a flea GABA receptor subunit protein or to effect flea GABA receptor subunit activity).

An isolated flea GABA receptor subunit nucleic acid molecule of the present invention can include a nucleic acid sequence that encodes at least one flea GABA receptor subunit protein of the present invention respectively, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea GABA receptor subunit protein.

A preferred nucleic acid molecule of the present invention, when administered to an animal, is capable of protecting that animal from flea infestation. As will be disclosed in more detail below, a nucleic acid molecule of the present invention can be, or encode, an antisense RNA, a molecule capable of triple helix formation, a ribozyme, or other nucleic acid-based drug compound. In additional embodiments, a nucleic acid molecule of the present invention can encode a protective protein (e.g., a flea GABA receptor subunit protein of the present invention), the nucleic acid molecule being delivered to the animal, for example, by direct injection (i.e, as a genetic vaccine or therapy) or in a vehicle such as a recombinant virus vaccine or therapy or a recombinant cell vaccine or therapy.

In one embodiment of the present invention, a preferred flea GABA receptor subunit nucleic acid molecule includes an isolated nucleic acid molecule that hybridizes under conditions that preferably allow less than or equal to 20% base pair mismatch, preferably under conditions that allow less than or equal to 10% base pair mismatch, preferably under conditions that allow less than or equal to 8% base pair mismatch, preferably under conditions that allow less than or equal to 5% base pair mismatch or preferably under conditions that allow less than or equal to 2% base pair mismatch with a nucleic acid molecule selected from the group consisting of SEQ ID NO:1, SEQ ID NO:3, SEQ ID NO:7, SEQ ID NO:8, SEQ ID NO:9, and/or SEQ ID NO:11.

One embodiment of the present invention includes a flea GABA receptor subunit nucleic acid molecule, wherein said nucleic acid molecule hybridizes under conditions comprising, (a) hybridizing in solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 69.6° C., to an isolated nucleic acid molecule selected from the group consisting of SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11. Additional preferred nucleic acid molecules of the present invention include oligonucleotides of an isolated nucleic acid molecule, wherein said nucleic acid molecule hybridizes under conditions comprising, (a) hybridizing in solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 69.6° C., to an isolated nucleic acid molecule selected from the group consisting of SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11, wherein said oligonucleotide comprises at least 35 nucleotides.

Additional preferred flea GABA receptor subunit nucleic acid molecules of the present invention include nucleic acid molecules comprising a nucleic acid sequence that is preferably at least 80%, preferably at least 90%, preferably at least 92%, preferably at least 95%, or preferably at least 98% identical to a nucleic acid sequence selected from the group consisting of SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11. Also preferred are fragments of any of such nucleic acid molecules. Percent identity as used herein is determined using the Needleman-Wunscb algorithm, available in the SEQLAB® sequence analysis software using default parameters.

One embodiment of the present invention is a nucleic acid molecule comprising all or part of nucleic acid molecules nCfGR$_{183}$, nCfGR$_{5503}$, nCfGR$_{1446}$, nCfGR$_{717}$, or allelic variants of these nucleic acid molecules. One preferred nucleic acid molecule of the present invention includes at least a portion of nucleic acid sequence SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits an immune response against a protein having an amino acid sequence SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

One embodiment of the present invention is a nucleic acid molecule comprising an isolated nucleic acid molecule having a nucleic acid sequence selected from the group consisting of: (a) a nucleic acid sequence selected from the group consisting of SEQ ID NO:1, SEQ ID NO:3, SEQ ID NO:4, SEQ ID NO:6, SEQ ID NO:7, SEQ ID NO:8, SEQ ID NO:9, and SEQ ID NO:11; and (b) a nucleic acid molecule having an at least 35 contiguous nucleotide portion identical in sequence to an at least 35 contiguous nucleotide portion of a nucleic acid sequence selected from the group consisting of SEQ ID NO:1, SEQ ID NO:3, SEQ ID NO:4, SEQ ID NO:6, SEQ ID NO:7, SEQ ID NO:8, SEQ ID NO:9, and SEQ ID NO:11.

In one embodiment, flea GABA receptor subunit nucleic acid molecule of the present invention encodes a protein that is at least 80%, preferably at least 90%, preferably at least 92%, preferably at least 95%, preferably at least 98%, preferably at least 99%, or preferably at least 100% identical to PCfGR$_{60}$, PCfGR$_{482}$, or PCfGR$_{239}$.

In one embodiment, a flea GABA receptor subunit nucleic acid molecule of the present invention encodes a protein having an amino acid sequence that is at least 95%, preferably at least 98%, preferably at least 99%, or preferably at least 100% identical to SEQ ID NO:2, SEQ ID NO:5, and/or SEQ ID NO:10. The present invention also includes a flea GABA receptor subunit nucleic acid molecule encoding a protein having at least a portion of SEQ ID NO:2, SEQ ID NO:5, and/or SEQ ID NO:10, as well as allelic variants of a nucleic acid molecule encoding a protein having these sequences, including nucleic acid molecules that have been modified to accommodate codon usage properties of the cells in which such nucleic acid molecules are to be expressed.

In another embodiment, a preferred flea GABA receptor subunit nucleic acid molecule of the present invention comprises a nucleic acid molecule comprising at least 35 nucleotides, preferably at least 40 nucleotides, preferably at least 45 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 400 nucleotides, preferably at least 450 nucleotides, preferably at least 500 nucleotides, preferably at least 550 nucleotides, preferably at least 600 nucleotides, preferably at least 650 nucleotides, preferably at least 700 nucleotides, preferably at least 750 nucleotides, preferably at least 1000 nucleotides, preferably at least 1500 nucleotides, preferably at least 1750 nucleotides, preferably at least 2000 nucleotides, preferably at least 2250 nucleotides, preferably at least 2500 nucleotides, preferably at least 2750 nucleotides preferably at least 3000 nucleotides, preferably at least 3500 nucleotides, preferably at least 4000 nucleotides, preferably at least 4500 nucleotides, preferably at least 5000 nucleotides or preferably at least 5500 nucleotides in length.

In another embodiment, a preferred flea GABA receptor subunit nucleic acid molecule encodes a protein comprising at least 180 amino acids, preferably at least 200 amino acids, preferably at least 225 amino acids, preferably at least 250 amino acids, preferably at least 300 amino acids, preferably at least 350 amino acids, preferably at least 400 amino acids, preferably at least 450 amino acids, preferably at least 475 amino acids, or preferably at least 480 amino acids.

In another embodiment, a preferred flea GABA receptor subunit nucleic acid molecule of the present invention comprises an apparently full-length flea GABA receptor subunit coding region, i.e., the preferred nucleic acid molecule encodes an apparently full-length flea GABA receptor subunit protein, respectively, or a post-translationally modified protein thereof. In one embodiment, a preferred flea GABA receptor subunit nucleic acid molecule of the present invention encodes a mature protein or extracellular domain.

In another embodiment, a preferred flea GABA receptor subunit nucleic acid molecule of the present invention comprises a nucleic acid molecule comprising SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11, or a fragment thereof.

A flea GABA receptor subunit nucleic acid molecule of the present invention preferably comprises at least 35 nucleotides, preferably at least 40 nucleotides, preferably at least 45 nucleotides, preferably at least 50 nucleotides, preferably at least 75 nucleotides, preferably at least 100 nucleotides, preferably at least 125 nucleotides, preferably at least 150 nucleotides, preferably at least 175 nucleotides, preferably at least 200 nucleotides, preferably at least 250 nucleotides, preferably at least 350 nucleotides, preferably at least 400 nucleotides, preferably at least 450 nucleotides, preferably at least 500 nucleotides, preferably at least 550 nucleotides, preferably at least 600 nucleotides, preferably at least 650 nucleotides, preferably at least 700 nucleotides, preferably at least 750 nucleotides, preferably at least 1000 nucleotides, preferably at least 1500 nucleotides, preferably at least 1750 nucleotides, preferably at least 2000 nucleotides, preferably at least 2250 nucleotides, preferably at least 2500 nucleotides, preferably at least 2750 nucleotides preferably at least 3000 nucleotides, preferably at least 3500 nucleotides, preferably at least 4000 nucleotides, preferably at least 4500 nucleotides, preferably at least 5000 nucleotides or preferably at least 5500 nucleotides identical in sequence to a corresponding contiguous sequence selected from the group consisting of SEQ ID NO:1, SEQ ID NO:3, SEQ ID NO:4, SEQ ID NO:6, SEQ ID NO:7, SEQ ID NO:8, SEQ ID NO:9, and/or SEQ ID NO:11.

The phrase, a nucleic acid molecule comprising at least "x" contiguous, or consecutive nucleotides identical in sequence to at least "x" contiguous, or consecutive nucleotides of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to a molecule of the present invention, as well as extensions that show similarity or identity to cited nucleic acids sequences or portions thereof.

Knowing the nucleic acid sequences of certain flea GABA receptor subunit nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other flea GABA receptor subunit nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include cDNA libraries as well as genomic DNA libraries. Similarly, preferred DNA sources to screen or from which to amplify nucleic acid molecules include cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising *C. felis* GABA receptor subunit nucleic acid molecules or other flea GABA receptor subunit nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably 100 to 200 nucleotides. The present invention includes oligonucleotides that can be used as, for example, probes to identify nucleic acid molecules, primers to produce nucleic acid molecules, or therapeutic reagents to inhibit flea GABA receptor subunit protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of flea GABA receptor subunit nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those that function in bacterial, yeast, or insect and mammalian cells, such as, but not limited to, tac, lac, trp, trc, oxy-pro, omp/lpp, rrnB, bacteriophage lambda (such as lambda $P_L$ and lambda $P_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virlis, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas, such as *C. felis* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nCfGR_{183}$, $nCfGR_{5503}$, $nCfGR_{1446}$, $nCfGR_{717}$.

Recombinant molecules of the present invention may also (a) contain secretory signals (i.e., signal segment nucleic acid sequences) to enable an expressed flea GABA receptor subunit protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include flea GABA receptor subunit nucleic acid molecules disclosed herein. Preferred nucleic acid molecules with which to transform a cell include $nCfGR_{183}$, $nCfGR_{5503}$, $nCfGR_{1446}$, $nCfGR_{717}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing flea GABA receptor subunit proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, insect and mammalian cells. More preferred host cells include *Salmonella, Escherichia, Bacillus, Caulobacter, Listeria, Saccharomyces, Pichia, Spodoptera, Mycobacteria, Trichoplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1 $_\chi$3987 and SR-11 $_\chi$4072; *Caulobacter; Pichia; Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/W3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including flea GABA receptor subunit nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated flea GABA receptor subunit proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a flea GABA receptor subunit protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea GABA receptor subunit protein of the present invention or a mimetope thereof (e.g., anti-flea GABA receptor subunit antibodies). As used herein, the term "selectively binds to" a protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-flea GABA receptor subunit antibody of the present invention preferably selectively binds to a flea GABA receptor subunit protein, respectively, in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce flea GABA receptor subunit proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from fleas susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to fleas in order to directly kill such fleas. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal susceptible to flea infestation, is capable of protecting that animal from flea infestation. Therapeutic compositions of the present invention include at least one of the following protective molecules: an isolated flea GABA receptor subunit protein; a mimetope of an isolated flea GABA receptor subunit protein; an isolated flea GABA receptor subunit nucleic acid molecule; and/or a compound derived from said isolated flea GABA receptor subunit protein that inhibits flea GABA receptor subunit protein activity, an anti-flea GABA receptor antibody, and/or a compound that inhibits flea GABA receptor activity. A therapeutic composition of the present invention can further comprise a component selected from the group of an excipient, a carrier, and/or an adjuvant; these components are described further herein. As used herein, a protective molecule or protective compound refers to a compound that, when administered to an animal in an effective manner, is able to treat, ameliorate, and/or prevent flea infestation. Preferred fleas to target are heretofore disclosed. One example of a protective molecule is a vaccine or therapy, such as, but not limited to, a naked nucleic acid vaccine or therapy, a recombinant virus vaccine or therapy, a recombinant cell vaccine or therapy, and a recombinant protein vaccine or therapy. Another example of a protective molecule is a compound that inhibits flea GABA receptor subunit protein activity, such as an isolated antibody that selectively binds to a flea GABA receptor subunit protein, a substrate analog of a flea GABA receptor subunit protein, anti-sense-, triplex formation-, ribozyme-, and/or RNA drug-based compounds, or other inorganic or organic molecules that inhibit flea GABA receptor subunit protein activity. Inhibiting flea GABA receptor subunit protein activity can refer to the ability of a compound to reduce the activity of flea GABA receptor subunit proteins. Inhibiting flea GABA receptor subunit protein activity can also refer to the ability of a compound to reduce the amount of flea GABA receptor subunit protein in a flea.

Another embodiment of the present invention includes a method to reduce flea infestation in an animal susceptible to flea infestation. Such a method includes the step of administering to the animal a therapeutic molecule comprising a protective compound selected from the group consisting of (a) an isolated flea GABA receptor subunit protein; (b) a mimetope of an isolated flea GABA receptor subunit protein; (c) an isolated flea GABA receptor subunit nucleic acid molecule; and (d) a compound derived from an isolated flea GABA receptor subunit protein that inhibits flea GABA receptor subunit protein activity.

Therapeutic compositions of the present invention can be administered to any animal susceptible to flea infestation, preferably to mammals, and more preferably to dogs, cats, humans, ferrets, horses, cattle, sheep, and other pets, economic food animals, work animals and/or zoo animals. Preferred animals to protect against flea infestation include dogs, cats, humans, and ferrets, with dogs and cats being particularly preferred.

As used herein, the term derived, or the term derived from, refers to a peptide, antibody, mimetope, nucleic acid molecule, or other compound that was obtained directly or indirectly from a flea GABA receptor subunit protein or nucleic acid molecule of the present invention, e.g. a part of a protein or nucleic acid molecule or produced using a protein or nucleic acid molecule of the present invention. Methods to obtain derivatives from a flea GABA receptor subunit molecule of the present invention are known in the art, and as such include, but are not limited to molecular modeling of flea GABA receptor subunit proteins to determine active sites, and predicting from these active sites smaller fragments and/or mimetopes that retain and/or mimic these active sites, thereby inhibiting flea GABA receptor subunit protein activity. Other inhibitors of flea GABA receptor subunit activity can also be obtained in a variety of ways, including but not limited to screening of peptide or small chemical compound libraries against flea GABA receptor subunit proteins of the present invention; and screening of polyclonal or monoclonal antibodies to find antibodies that specifically bind flea GABA receptor subunit proteins of the present invention.

A flea GABA receptor subunit protein inhibitor of the present invention (i.e. an inhibitor of a flea GABA receptor subunit protein) is identified by its ability to mimic, bind to, modify, or otherwise interact with, a flea GABA receptor subunit protein, thereby inhibiting the activity of a natural flea GABA receptor subunit protein. Suitable inhibitors of flea GABA receptor subunit protein activity are compounds that can inhibit flea GABA receptor subunit protein activity in at least one of a variety of ways: (a) by binding to or otherwise interacting with or otherwise modifying flea GABA receptor subunit protein sites; (b) by binding to or otherwise interacting with or otherwise modifying the flea GABA receptor subunit protein active site; (c) by binding to the flea GABA receptor subunit protein and thus reducing the availability of the flea GABA receptor subunit protein in solution; (d) by mimicking a flea GABA receptor subunit protein; and (e) by interacting with other regions of the flea GABA receptor subunit protein to inhibit flea GABA receptor subunit protein activity, for example, by allosteric interaction.

Flea GABA receptor subunit protein inhibitors can be used directly as compounds in compositions of the present invention to treat animals as long as such compounds are not harmful to host animals being treated. Preferred flea GABA receptor subunit protein inhibitors of the present invention include, but are not limited to, flea GABA receptor subunit protein substrate analogs, and other molecules that bind to a flea GABA receptor subunit protein (e.g., to an allosteric site) in such a manner that the activity of the flea GABA receptor subunit protein is inhibited. A flea GABA receptor subunit protein substrate analog refers to a compound that interacts with (e.g., binds to, associates with, modifies) the active site of a flea GABA receptor subunit protein. A preferred flea GABA receptor subunit protein substrate analog inhibits flea GABA receptor subunit protein activity. Flea GABA receptor subunit protein substrate analogs can be of any inorganic or organic composition. Flea GABA receptor subunit protein substrate analogs can be, but need not be, structurally similar to a flea GABA receptor subunit protein natural substrate as long as they can interact with the active site of that flea GABA receptor subunit protein. Flea GABA receptor subunit protein substrate analogs can be designed using computer-generated structures of flea GABA receptor subunit proteins of the present invention or computer structures of flea GABA receptor subunit protein's natural substrates. Preferred sites to model include one or more of the active sites of flea GABA receptor subunit proteins. Substrate analogs can also be obtained by generating random samples of molecules, such as oligonucleotides, peptides, peptidomimetic compounds, or other inorganic or organic molecules, and screening such samples for their ability to interfere with interaction between flea GABA receptor subunit proteins and their substrates, e.g. by affinity chromatography techniques. A preferred flea GABA receptor subunit protein substrate analog is a flea GABA receptor subunit protein mimetic compound, i.e., a compound that is structurally and/or functionally similar to a natural substrate of a flea GABA receptor subunit protein of the present invention, particularly to the region of the substrate that interacts with the flea GABA receptor subunit protein active site, but that inhibits flea GABA receptor subunit protein activity upon interacting with the flea GABA receptor subunit protein active site.

The present invention also includes a therapeutic composition comprising at least one protective molecule of the present invention in combination with at least one additional compound protective against one or more infectious agents.

In one embodiment, a therapeutic composition of the present invention can be used to protect an animal from flea infestation by administering such composition to a flea in order to prevent infestation. Such administration to the flea and/or animal could be oral, or by application to the animal's body surface (e.g. topical spot-on, or spraying onto the animal), or by application to the environment (e.g., spraying). Examples of such compositions include, but are not limited to, transgenic vectors capable of producing at least one therapeutic composition of the present invention. In another embodiment a flea can ingest therapeutic compositions, or products thereof, present on the surface of or in the blood of a host animal that has been administered a therapeutic composition of the present invention.

In accordance with the present invention, a host animal (i.e., an animal that is or is capable of being infested with fleas) is treated by administering to the animal a therapeutic composition of the present invention in such a manner that the composition itself (e.g., a flea GABA receptor subunit protein inhibitor, a GABA receptor subunit protein synthesis suppressor (i.e., a compound that decreases the production or half-life of a GABA receptor subunit protein in fleas), a flea GABA receptor subunit protein mimetope, or a anti-flea GABA receptor subunit antibody) or a product generated by the animal in response to administration of the composition (e.g., antibodies produced in response to administration of a flea GABA receptor subunit protein or nucleic acid molecule, or conversion of an inactive inhibitor "prodrug" to an active flea GABA receptor subunit protein inhibitor) ultimately enters the flea. A host animal is preferably treated in such a way that the compound or product thereof is present on the body surface of the animal or enters the blood stream of the animal. Fleas are then exposed to the composition or product when they feed from the animal. For example, flea flea GABA receptor subunit protein inhibitors administered to an animal are administered in such a way that the inhibitors enter the blood stream of the animal, where they can be taken up by feeding fleas.

The present invention also includes the ability to reduce larval flea infestation in that when fleas feed from a host animal that has been administered a therapeutic composition of the present invention, at least a portion of compounds of the present invention, or products thereof, in the blood taken up by the fleas are excreted by the fleas in feces, which is subsequently ingested by flea larvae. In particular, it is of note that flea larvae obtain most, if not all, of their nutrition from flea feces.

In accordance with the present invention, reducing flea GABA receptor subunit protein activity in a flea can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal, (g) altering the development of flea larvae (e.g., by decreasing feeding behavior, inhibiting growth, inhibiting (e.g., slowing or blocking) molting, and/or otherwise inhibiting maturation to adults), and/or (h) altering or decreasing the ability of fleas or flea larvae to digest a blood meal.

In order to protect an animal from flea infestation, a therapeutic composition of the present invention is administered to the animal in an effective manner such that the composition is capable of protecting that animal from flea infestation. Therapeutic compositions of the present invention can be administered to animals prior to infestation in order to prevent infestation (i.e., as a preventative vaccine) and/or can be administered to animals after infestation (i.e. as a therapy). For example, proteins, mimetopes thereof, and antibodies thereof can be used as immunotherapeutic agents.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), Flt-3 ligand, granulocyte colony stimulating factor (G-CSP), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I(IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's TITERMAX™ adjuvant (VAXCEL™ adjuvant, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle.

Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition. The therapeutic composition is preferably released over a period of time ranging from about 1 to about 12 months. A controlled release formulation of the present invention is capable of effecting a treatment preferably for at least 1 month, more preferably for at least 3 months, even more preferably for at least 6 months, even more preferably for at least 9 months, and even more preferably for at least 12 months.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of treating an animal when administered one or more times over a suitable time period. For example, a preferred single dose of an inhibitor is from about 1 microgram (μg) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 μg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, intraocular, intranasal, conjunctival, and intramuscular routes. Methods of administration for other therapeutic compounds can be determined by one skilled in the art, and may include administration of a therapeutic composition one or more times, on a daily, weekly, monthly or yearly regimen; routes of administration can be determined by one skilled in the art, and may include any route. A preferred route of administration of an inhibitory compound when administering to fleas is a topical, or "spot-on" formulation administered to the body surface of the animal, so that a flea would encounter the inhibitory compound when attached to the animal; another preferred route of administration of an inhibitory compound is an oral formulation that, when fed to an animal, would enter the bloodstream of the animal, which would then be transferred to a flea while feeding from the animal.

A recombinant protein vaccine or therapy of the present invention comprises a recombinantly-produced flea GABA receptor subunit protein of the present invention that is administered to an animal according to a protocol that results in the animal producing a sufficient immune response to protect itself from a flea infestation. Such protocols can be determined by those skilled in the art.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine or therapy (e.g., as naked DNA or RNA molecules, such as is taught, for example in Wolff et al., 1990, *Science* 247, 1465-1468) or (b) administering a nucleic acid molecule packaged as a recombinant virus vaccine or therapy or as a recombinant cell vaccine or therapy (i.e., the nucleic acid molecule is delivered by a viral or cellular vehicle).

A genetic (i.e., naked nucleic acid) vaccine or therapy of the present invention includes a nucleic acid molecule of the present invention and preferably includes a recombinant molecule of the present invention that preferably is replication, or otherwise amplification, competent. A genetic vaccine or therapy of the present invention can comprise one or more nucleic acid molecules of the present invention in the form of, for example, a dicistronic recombinant molecule. Preferred genetic vaccine or therapys include at least a portion of a viral genome, i.e., a viral vector. Preferred viral vectors include those based on alphaviruses, poxviruses, adenoviruses, herpesviruses, picornaviruses, and retroviruses, with those based on alphaviruses, such as sindbis or Semliki forest virus, species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines or therapies of the present invention can be administered in a variety of ways, with intramuscular, subcutaneous, intradermal, transdermal, conjunctival, intraocular, intranasal and oral routes of administration being preferred. A preferred single dose of a genetic vaccine ranges from about 1 nanogram (ng) to about 600 μg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine or therapy of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines or therapies are those based on alphaviruses (such as Sindbis virus), raccoon poxviruses, species-specific herpesviruses and species-specific poxviruses. An example of methods to produce and use alphavirus recombinant virus vaccines are disclosed in U.S. Pat. No. 5,766,602 to Xiong and Grieve, which is incorporated by reference herein in its entirety.

When administered to an animal, a recombinant virus vaccine or therapy of the present invention infects cells within the immunized animal and directs the production of a protective protein or RNA nucleic acid molecule that is capable of protecting the animal from flea infestation as disclosed herein. For example, a recombinant virus vaccine or therapy comprising a flea GABA receptor subunit nucleic acid molecule of the present invention is administered according to a protocol that results in the animal producing a sufficient immune response to protect itself from flea infestation. A preferred single dose of a recombinant virus vaccine or therapy of the present invention is from about $1\times10^4$ to about $1\times10^8$ virus plaque forming units (pfu) per kilogram body weight of the animal. Administration protocols are similar to those described herein for protein-based vaccines or therapies, with subcutaneous, intramuscular, intranasal, intraocular, conjunctival, and oral administration routes being preferred.

A recombinant cell vaccine or therapy of the present invention includes recombinant cells of the present invention that express at least one protein of the present invention. Preferred recombinant cells for this embodiment include *Salmonella*, *E. coli*, *Listeria*, *Mycobacterium*, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines or therapies of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines or therapies. Recombinant cell vaccines or therapies can comprise whole cells, cells stripped of cell walls or cell lysates.

The efficacy of a therapeutic composition of the present invention to protect an animal from flea infestation can be tested in a variety of ways including, but not limited to, detection of protective antibodies (using, for example, proteins or mimetopes of the present invention), detection of cellular immunity within the treated animal, or challenge of the treated animal with the fleas to determine whether the treated animal is resistant to infestation. Challenge studies can include direct administration of fleas to the treated animal. In one embodiment, therapeutic compositions can be tested in animal models such as mice. Such techniques are known to those skilled in the art.

As discussed herein, one therapeutic composition of the present invention includes an inhibitor of flea GABA receptor subunit protein activity, i.e., a compound capable of substantially interfering with the function of a flea GABA receptor subunit protein. An inhibitor of flea GABA receptor subunit protein activity, or function, can be identified using flea GABA receptor subunit proteins of the present invention. A preferred inhibitor of flea GABA receptor subunit protein function is a compound capable of substantially interfering with the function of a flea GABA receptor subunit protein and which does not substantially interfere with the function of host animal GABA receptor subunit proteins. As used herein, a compound that does not substantially inhibit or interfere with host animal GABA receptor subunit proteins is one that, when administered to a host animal, the host animal shows no significant adverse effects attributable to the inhibition of GABA receptor subunit and which, when administered to an animal in an effective manner, is capable of protecting that animal from flea infestation.

One embodiment of the present invention is a method to identify a compound capable of inhibiting flea GABA receptor subunit protein activity. Such a method includes the steps of (a) contacting (e.g., combining, mixing) an isolated flea GABA receptor subunit protein of the present invention, with a putative inhibitory compound under conditions in which, in the absence of the compound, the protein has flea GABA receptor subunit protein activity, and (b) determining if the putative inhibitory compound inhibits the activity. Flea GABA receptor subunit protein activity can be determined in a variety of ways known in the art, including but not limited to determining the ability of flea GABA receptor subunit protein to bind to or otherwise interact with a substrate. Such conditions under which a flea GABA receptor subunit protein has flea GABA receptor subunit protein activity include conditions in which a flea GABA receptor subunit protein has a correct three-dimensionally folded structure under physiologic conditions, i.e. physiologic pH, physiologic ionic concentrations, and physiologic temperatures.

Putative inhibitory compounds to screen include antibodies (including fragments and mimetopes thereof), putative substrate analogs, and other, preferably small, organic or inorganic molecules. Methods to determine flea GABA receptor subunit protein activity are known to those skilled in the art.

A preferred method to identify a compound capable of inhibiting flea GABA receptor subunit protein activity includes contacting an isolated flea GABA receptor subunit protein of the present invention with a putative inhibitory compound under conditions in which, in the absence of the compound, the protein has flea GABA receptor subunit protein activity; and determining if the putative inhibitory compound inhibits the activity.

Another embodiment of the present invention is an assay kit to identify an inhibitor of a flea GABA receptor subunit protein of the present invention. This kit comprises an isolated flea GABA receptor subunit protein of the present invention, and a means for determining inhibition of an activity of flea GABA receptor subunit protein, where the means enables detection of inhibition. Detection of inhibition of flea GABA receptor subunit protein identifies a putative inhibitor to be an inhibitor of a flea GABA receptor subunit protein. Means for determining inhibition of a flea GABA receptor subunit protein include, for example, an assay system that detects binding of a putative inhibitor to a flea GABA receptor subunit molecule, and an assay system that detects interference by a putative inhibitor of the ability of flea GABA receptor subunit protein to bind GABA. Means and methods are described herein and are known to those skilled in the art.

One embodiment of the present invention is a method to identify the presence of a GABA receptor genotype in an individual flea or in a flea population which conveys resistance to insecticides. Such a method includes the steps of (a) isolating a flea GABA receptor subunit nucleic acid molecule of the present invention from one or more fleas, (b) determining the nucleic acid sequence of such a nucleic acid molecule, and (c) determining if the nucleic acid sequence contains one or more known insecticide-resistance genes or determining the presence of mutant genes not formerly known to the population. In one embodiment, such a method includes determining both alleles which encode a protein with SEQ ID NO:5 and determining whether each allele encodes a serine or an alanine at amino acid 285 of SEQ ID NO:5, which the inventors were first to identify and correlate with cyclodiene resistance in fleas. A preferred method for isolating a flea GABA receptor subunit nucleic acid molecule of the present invention includes using primers and probes designed using a flea GABA receptor subunit nucleic acid sequence of the present invention. Techniques for isolating and determining the sequence of nucleic acid molecules are known to those of skill in the art.

One embodiment of the present invention is a method to design or identify an inhibitor of flea GABA receptor subunit activity using a nucleic acid molecule of the present invention. Such a method includes the steps of (1) identifying one or more insecticide-resistance loci of a flea GABA receptor subunit protein and (2) designing or identifying a compound which is unaffected by the insecticide-resistance locus or loci. This embodiment includes a method of screening compounds by contacting a compound alternatively with fleas having one or more insecticide-resistance loci and fleas without such an insecticide-resistance locus or loci and determining whether the ability of the compound to kill fleas is affected by the insecticide-resistance locus or loci.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLE 1

This example describes the isolation and characterization of a flea GABA receptor subunit nucleic acid molecule of the present invention from a flea mixed-instar cDNA library.

A. A flea GABA receptor subunit nucleic acid molecule of about 183 nucleotides was isolated from a flea mixed-instar cDNA library, prepared as described in PCT publication WO 99/3 1253, published Jun. 24, 1999 and incorporated herein by reference, in a nested PCR amplification as follows, In a first PCR reaction, degenerate sense primer GABASen, having a nucleotide sequence 5'ATG GAT TTY ACA YTG GAY TTY TAY 3', denoted SEQ ID NO:12 was used in combination with reverse primer T7, having a nucleic acid sequence 5'TAA TAC GAC TCA CTA TAG GO 3', denoted SEQ TD NO: 13, using 2 µl of the flea mixed-instar cDNA library as the template under the following PCR reaction and thermocycling conditions: (1) one cycle of 95° C. for 10 minutes; (2) five cycles of 95° C. for 15 seconds, 43° C. for 20 seconds, and 72° C. for 60 seconds; and (3) thirty cycles of 95° C. for 15 seconds, 46° C. for 15 seconds and 72° C. for 75 seconds, in a reaction containing 2.5 units of AMPLITAQ GOLD® DNA polymerase, available from Perkin Elmer, Norwalk, Conn., 1× Gold AMPLITAQ GOLD® PCR buffer, 0.2 mM dNTP's, 2.0 µM each primer in 50 µl reaction volumes, referred to hereinafter as "standard PCR reaction conditions".

Sense primer GABASen (described above) and degenerate reverse primer GABArev, having a nucleotide sequence 5'ATT NAK CCA RAA TGA WAC CCA 3', denoted SEQ ID NO:14, were used to conduct a second, hemi-nested PCR reaction as follows. The second reaction was conducted using the first PCR reaction products as the template under standard reaction conditions with the exception of the use of AMPLITAQ® DNA polymerase and AMPLITAQ® PCR buffer, available from Clontech Laboratories, Inc., Palo Alto, Calif., rather than AMPLITAQ® GOLD, under the following cycling conditions (1) one cycle of 95° C. 30 sec, (2) thirty-five cycles of 95° C. 15 sec, 42° C. 15 sec, 72° C. min and (3) one cycle of 5 minutes at 72° C.

Sequence information obtained from a product amplified in the second PCR reaction was used to design sense primer GABAnestFor, having a nucleotide sequence 5' AAA CAT ATG GGT CCC TGA CAC 3', denoted SEQ ID NO:15, and reverse primer GABAnestRev, having a nucleotide sequence 5' TAT CGC GCA TCG TGT AGC CG 3', denoted SEQ ID NO:16. The reaction product from the second PCR reaction was used as the template in a third PCR reaction, conducted under standard reaction conditions, with the exception of the use of 1 µl of template, under the following cycling conditions (1) one cycle of 95° C. 30 sec, (2) thirty cycles of 95° C. 15 sec, 50° C. 15 sec, 72° C. 1 min and (3) one cycle of 5 minutes at 72° C. A 183-nucleotide fragment, denoted nCfGR$_{183}$, having a coding strand designated SEQ ID NO:1 and a complementary strand designated SEQ ID NO:3, was isolated, T/A cloned using a TOPO™ T/A cloning kit, available from Invitrogen, Carlsbad, Calif., and shown to encode a partial length protein of 60 amino acids, designated PCfGR$_{60}$ and denoted herein as SEQ ID NO:2, assuming a first codon spanning from nucleotide 1 through nucleotide 3 of SEQ ID NO:1 and a last codon spanning from nucleotide 181 through nucleotide 183 of SEQ ID NO:1.

B. Nucleic acid molecule nCfGR$_{183}$ was $^{32}$P α-dATP labeled and used as a probe in a standard plaque lift hybridization procedure to isolate a flea GABA receptor nucleic acid molecule from a wandering larval flea cDNA library, prepared as described in PCT publication WO 99/31253, ibid. The following hybridization conditions were used: filters were hybridized with about 1×10$^6$ counts per minute (cpm) per ml of the probe in 5×SSPE, (see Sambrook et al., ibid.), 1% sarcosyl, 0.1% nonfat dry milk and 5× Denhardt's reagent, (see Sambrook et al., ibid.), at 45° C. for about 29 hours. Following hybridization, two washes were performed in 0.5×SSPE, 0.1% sarcosyl at 55° C. for about 20 minutes for the first wash and 15 minutes for the second wash. One positive plaque that hybridized strongly to the probe was carried through successive plaque screening until plaque purity was achieved then subjected to in vivo excision. In vivo excision was performed using the EX-ASSIST™ helper phage system and protocols, available from Stratagene, La Jolla, Calif. to convert a positive plaque to pBLUESCRI-IPT™ plasmid DNA. Sequencing was conducted using an ABI PRISM® 377 automatic DNA Sequencer, available from Perkin Elmer, following preparation of DNA with a QUANTUM PREP® plasmid Kit, available from Rio Rad, Hercules, Calif., using the manufacturer's instructions.

The resulting plasmid contained a nucleic acid molecule of about 5503 base pairs, referred to herein as nCfGR$_{5503}$, the coding strand of which is denoted herein as SEQ ID NO:4. The complement of SEQ ID NO:4 is represented herein as SEQ ID NO:6. Translation of SEQ ID NO:4 suggests that nucleic acid molecule nCfGR$_{5503}$ encodes a full-length flea GABA receptor subunit protein of 482 amino acids, referred to herein as PCfGR$_{482}$, having an amino acid sequence represented by SEQ ID NO:5, assuming the initiation codon spans from nucleotide 378 through nucleotide 380 of SEQ ID NO:4 and the termination codon spans from nucleotide 1824 through nucleotide 1826 of SEQ ID NO:4. The coding region encoding PCfGR$_{482}$, is represented by nucleic acid molecule nCfGR$_{1446}$, having a coding strand with the nucleic acid sequence represented by SEQ ID NO:7 and a complementary strand with nucleic acid sequence represented by SEQ ID NO:8. The amino acid sequence of PCfGR$_{482}$, predicts that PCfGR$_{482}$ has an estimated molecular weight of about 53.7 kilodaltons (kDa) and an estimated isoelectric point (pI) of about 9.6.

Comparison of amino acid sequence SEQ ID NO:5 with amino acid sequences reported in the GENBANK® sequence database indicates that SEQ ID NO:5 showed the most homology, i.e., about 88% identity, with the protein product of a *Lucilia cuprina* gamma-aminobutyric acid receptor subunit (Rdl) mRNA, GENBANK® sequence database Accession No. AF024647. Comparison of SEQ ID NO:7 with nucleic acid sequences reported in the GENBANK® sequence database indicates that SEQ ID NO:7 showed the most homology, i.e., about 75% identity, with a *Lucilia cuprina* gamma-aminobutyric acid receptor subunit (Rdl) mRNA nucleic acid molecule, GENBANK® sequence database Accession number AF024647. Percent identity calculations were performed by pair-wise comparison with the Needleman-Wunsch algorithm, available in the SEQLAB® sequence analysis software, using the Pairwise Comparison/ Gap function with the nwsgapdna.cmp scoring matrix, the gap creation penalty and the gap extension penalties set at default values, and the gap shift limits set at maximum.

EXAMPLE 2

The following example describes the expression of an extracellular domain of a flea GABA receptor subunit nucleic acid molecule of the present invention.

A portion of the N-terminus of SEQ ID NO:4 thought to contain the extracellular domain of the protein was produced as follows. A PCR reaction was performed using SEQ ID NO:4 as template with forward primer GABA5Met, having a nucleotide sequence 5' GGG CTC GAG CAT GGC GGC GCT GAC TCG C 3', having an XhoI site shown in bold, designated herein as SEQ ID NO:17, and reverse primer EXP3R1, having a nucleotide sequence 5' ATT GAA TTC TTA GGG AGA ATA GTT TCC TGT TGT GAG A 3', having an EcoRI site shown in bold, designated herein as SEQ ID NO:18, under standard PCR reaction conditions with the exception that 20 ng of template and Advantage 2 polymerase, available from Clontech, were used. The thermocycling conditions for this reaction are as follows: (1) one cycle of 95° C. for 60 seconds; (2) five cycles of 94° C. for 10 seconds, 49° C. for 40 seconds, and 69° C. for 60 seconds; and (3) twenty-seven cycles of 94° C. for 10 seconds, 52° C. for 20 seconds, and 69° C. for 90 seconds. This PCR reaction created a PCR product encoding the putative flea GABA receptor subunit extracellular domain (i.e. nucleotides 377 through 1095 of SEQ ID NO:4), denoted herein as nCfGR$_{717}$, having a coding strand with a nucleic acid sequence designated SEQ ID NO:9 and a complementary strand with a nucleic acid sequence designated SEQ ID NO:11, flanked by XhoI and EcoRI restriction sites. Translation of SEQ ID NO:9 suggests that nucleic acid molecule nCfGR$_{717}$ encodes a partial-length flea GABA receptor subunit protein of 239 amino acids, referred to herein as PCfGR$_{239}$, having an amino acid sequence represented by SEQ ID NO:10, assuming the initiation codon spans from nucleotide 2 through nucleotide 4 of SEQ ID NO:9 and the last codon spans from nucleotide 716 through nucleotide 718 of SEQ ID NO:9.

The product from the PCR reaction described above was separated on an agarose gel, excised, purified using a QIAQUICK® PCR purification kit, available from Qiagen, Valencia, Calif., digested with XhoI and EcoRI restriction enzymes and ligated into the λcro plasmid vector, the production of which is described in U.S. Pat. No. 5,569,603 by Tripp et al., issued Oct. 29, 1996, that had been digested by XhoI and EcoRI and gel purified to produce recombinant molecule pλcro-nCfGR$_{717}$. The insert in the recombinant molecule was verified by DNA sequencing. Recombinant molecule pλcro-nCfGR$_{717}$ was used to transform E. coli strain (BL21), thereby producing BL21-pλcro-nCfGR$_{717}$. Cells were allowed to grow in LB media with 100 µg/ml ampicillin at 32° C. until an OD$_{600}$ of 0.5 was reached. Production of protein PCfGR$_{239}$ was induced by shifting the temperature to 42 ° C. and incubating for an additional 2-3 hours. Cells were chilled and then harvested by centrifugation at 6000×g for 30 mm in an IEC model PR-7000M refrigerated large volume centrifuge, available from International Equipment Company, Needham Heights, Mass. Induced cell lysates were run on an SDS-PAGE gel, proteins were transferred to nitrocellulose, and a band of ~28 kDa was recognized by an anti T-7 TAG® monoclonal antibody, available from Novagen, Madison, Wis. Comparison of amino acid sequence SEQ ID NO:10 with amino acid sequences reported in GenBank indicates that SEQ ID NO:10 showed the most homology, i.e., about 91% identity, with the protein product of a Drosophila melanogaster Rdl gene, GenBank AAF50311. Comparison of amino acid sequence SEQ ID NO:9 with amino acid sequences reported in the GENBANK® sequence database indicates that SEQ ID NO:9 showed the most homology, i.e., about 75% identity, with a Lucilia cuprina gamma-aminobutyric acid receptor subunit (Rdl) mRNA nucleic acid molecule, GENBANK® sequence database Accession number AF024647.

EXAMPLE 3

This example describes sequencing of DNA derived from individual fleas to determine the presence of allelic variants within a given individual.

The DNA from individual fleas from several different populations was sequenced and analyzed. Analysis of these sequences revealed the presence of allelic variants at certain nucleotides encoding amino acid positions 278 and 285 of SEQ ID NO:5. Amino acid 278 may be either N or H, due to a variation between adenine and cytosine at nucleotide position 832 of SEQ ID NO:7. Amino acid 285 may be either S or A due to a variation between thymine and guanine at nucleotide position 853 of SEQ ID NO:7. The variation at amino acid 285 is believed to be homologous to the Serine to Alanine variation seen in D. melanogaster GABA receptor at amino acid 302, which has been linked to resistance to cylcodienes.

The following method was used to determine the genotype of individual fleas. Individual fleas were physically crushed with a pipette tip in a microcentrifuge tube with 30 µl of DNAZOL®, available from Gibco BRL, Rockville, Md., then heated to 95° C. for 5 minutes. The mixture was centrifuged for 2 minutes, the liquid was removed and DNA was precipitated with ethanol. The precipitated DNA was centrifuged, the ethanol was removed and the pellet was resuspended in 30 µl of distilled water. Five µl of suspended DNA was used in a PCR reaction with forward primer 285for, having a nucleic acid sequence 5'TAT AAA CTA GCG AAC AAC ATT AC 3', designated herein as SEQ ID NO:19, and reverse primer 285rev, having a nucleic acid sequence 5'GAT TCA ATT CUT GCG TTC TAT G 3', designated herein as SEQ ID NO:20. The following PCR thermocycling and reaction conditions were used (1) one cycle of 95° C. for 30 seconds, (2) 35 cycles of 94° C. for 10 seconds, 52° C. for 30 seconds, and 72° C. 30 seconds, in reactions containing 1× AMPLITAQ® PCR Buffer, 2.0 U AMPLITAQ® DNA polymerase, available from Perkin Elmer, Foster City, Calif., 0.2 mM dNTP's, and 0.5 uM each primer.

The PCR product was separated by gel electrophoresis and purified using a QIAQUICK® PCR purification kit, available from Qiagen to produce an approximately 240-nucleotide molecule. The 240-nucleotide product was then sequenced using primers 285for and 285rev and dRhodamine terminator chemistry and the sequence was read to determine whether the individual was homozygous for serine or alanine, or a heterozygote.

EXAMPLE 4

This example describes exposing fleas to various concentrations of the cyclodiene insecticide dieldrin, observing mortality rates among the exposed fleas, sequencing the DNA of individual fleas and correlating the mortality rates to genotype.

Three different colonies of fleas were assessed for their GABA receptor population genotype at amino acid 285, as described in Example 3. The three populations were found to be homozygous serine, homozygous alanine, and heterozygous at amino acid 285.

Dieldrin was dissolved in dimethylsulfoxide (DMSO) at concentrations ranging from 0.001 mM to 1000 mM. About 1 µl of dissolved dieldrin from each concentration was spotted onto a 6 mm diameter GF/C filter disk (Whatman, Inc. Clifton, N.J.) in the bottom of a 4 ml screw-top glass vial and allowed to air dry for 24 hours. Negative control vials were prepared in the same manner except that no dieldrin was dissolved in the DMSO. Each dieldrin concentration was tested in triplicate for each of the three flea populations. About 25 newly emerged cat fleas were sedated at 4° C. and transferred to each vial. Each vial was sealed with a thin, perforated Teflon septum secured by an open top screw cap and held vertically in the dark. After about 30 hours, the healthy live, moribund, and dead fleas in each vial were counted. The percentage of dead fleas in each vial was then calculated using the formula M=100(D−(FC/100)/(F−(FC/100)), in which M is the percentage of dead fleas due to the addition of dieldrin, D is the number of dead fleas in the dieldrin-containing vial, F is the total number of fleas in the dieldrin-containing vial, and C is the percentage of dead fleas in the negative control vial. The dieldrin $LC_{50}$, defined as the concentration of dieldrin at which 50% of the fleas were killed, was determined for each flea population. The $LC_{50}$ for the homozygous serine flea population was 30 mM, the $LC_{50}$ for the heterozygous alanine/serine flea population was 1.0 mM, and the $LC_{50}$ for the homozygous alanine flea population was 0.2 mM. In addition, fleas from the heterozygous population which were exposed to 10 mM and 50 mM of dieldrin were sequenced and the data was pooled to yield the following results. Of 21 fleas that were homozygous serine, 16 were live, 1 was moribund, and 4 were dead; of 29 heterozygotes 2 were live, 3 were moribund, and 24 were dead; of 1 homozygous alanine, 1 was dead. These results indicate that resistance to dieldrin in fleas due to variation at position 285 of SEQ ID NO:5 appears to correlate to the well-known resistance described for *D. melanogaster* due to a serine to alanine variation at position 302, as described by ffrench-Constant, ibid.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule selected from the group consisting of:
   (a) a nucleic acid molecule comprising a nucleic acid sequence that encodes SEQ ID NO:5 or SEQ ID NO:10;
   (b) a nucleic acid molecule fully complementary in sequence to the nucleic acid molecule of (a).

2. The isolated nucleic acid molecule of claim 1, wherein said nucleic acid sequence consists of SEQ ID NO:4 or SEQ ID NO:9.

3. An isolated nucleic acid molecule that consists of a nucleic acid sequence selected from the group consisting of:
   (a) a nucleic acid sequence that encodes SEQ ID NO:5 or SEQ ID NO: 10;
   (b) a nucleic acid sequence fully complementary to the nucleic acid sequence of (a).

4. The isolated nucleic acid molecule of claim 3, wherein said nucleic acid sequence consists of SEQ ID NO:4 or SEQ ID NO:9.

* * * * *